US008822673B2

(12) United States Patent
Chou et al.

(10) Patent No.: US 8,822,673 B2
(45) Date of Patent: *Sep. 2, 2014

(54) METHODS OF USING FET LABELED OLIGONUCLEOTIDES THAT INCLUDE A 3'-5' EXONUCLEASE RESISTANT QUENCHER DOMAIN AND COMPOSITIONS FOR PRACTICING THE SAME

(75) Inventors: Quin Chou, Camarillo, CA (US); Dragan Spasic, Daly City, CA (US)

(73) Assignee: Life Technologies Corporation, Carlsbad, CA (US)

( * ) Notice: Subject to any disclaimer, the term of this patent is extended or adjusted under 35 U.S.C. 154(b) by 190 days.

This patent is subject to a terminal disclaimer.

(21) Appl. No.: 12/945,777

(22) Filed: Nov. 12, 2010

(65) Prior Publication Data
US 2012/0245334 A1    Sep. 27, 2012

Related U.S. Application Data

(63) Continuation of application No. 12/786,194, filed on May 24, 2010, now Pat. No. 8,088,583, which is a continuation of application No. 12/197,739, filed on Aug. 25, 2008, now Pat. No. 7,754,453, which is a continuation of application No. 11/530,915, filed on Sep. 12, 2006, now abandoned, which is a continuation of application No. 11/198,924, filed on Aug. 4, 2005, now abandoned, which is a continuation of application No. 10/222,943, filed on Aug. 15, 2002, now Pat. No. 7,160,997, which is a continuation-in-part of application No. 10/087,229, filed on Feb. 27, 2002, now Pat. No. 6,818,420.

(51) Int. Cl.
*C07H 19/04* (2006.01)
*C07H 21/04* (2006.01)

(52) U.S. Cl.
USPC .................. 536/26.6; 536/23.1; 536/24.3

(58) Field of Classification Search
USPC ....................... 536/26.6, 23.1, 24.3
See application file for complete search history.

(56) References Cited

U.S. PATENT DOCUMENTS

| 4,743,535 A | 5/1988 | Carrico |
| 4,794,073 A | 12/1988 | Dattagupta et al. |

(Continued)

FOREIGN PATENT DOCUMENTS

| EP | 1275735 | 1/2003 |
| EP | 1952792 A1 | 8/2008 |

(Continued)

OTHER PUBLICATIONS

U.S. Appl. No. 09/177,387, filed Oct. 23, 1998, Hartley, James L.

(Continued)

*Primary Examiner* — Jezia Riley

(57) ABSTRACT

Methods and compositions are provided for detecting a primer extension product in a reaction mixture. In the subject methods, a primer extension reaction is conducted in the presence of a polymerase having 3'→5' exonuclease activity and at least one FET labeled oligonucleotide probe that includes a 3'→5' exonuclease resistant quencher domain. Also provided are systems and kits for practicing the subject methods. The subject invention finds use in a variety of different applications, and are particularly suited for use in high fidelity PCR based reactions, including SNP detection applications, allelic variation detection applications, and the like.

20 Claims, 19 Drawing Sheets

(56) References Cited

U.S. PATENT DOCUMENTS

| | | | |
|---|---|---|---|
| 4,950,744 | A | 8/1990 | Albarella et al. |
| 5,177,196 | A | 1/1993 | Meyer et al. |
| 5,419,966 | A | 5/1995 | Reed et al. |
| 5,475,610 | A | 12/1995 | Atwood et al. |
| 5,538,848 | A | 7/1996 | Livak et al. |
| 5,538,871 | A | 7/1996 | Nuovo |
| 5,602,756 | A | 2/1997 | Atwood |
| 5,612,473 | A | 3/1997 | Wu et al. |
| 5,691,146 | A | 11/1997 | Mayrand |
| 5,801,155 | A | 9/1998 | Kutyavin et al. |
| 5,824,796 | A | 10/1998 | Petrie et al. |
| 5,840,493 | A | 11/1998 | Davis et al. |
| 5,846,729 | A | 12/1998 | Wu et al. |
| 5,866,336 | A | 2/1999 | Nazarenko et al. |
| 5,955,590 | A | 9/1999 | Levina |
| 5,989,823 | A | 11/1999 | Jayasena |
| 6,072,046 | A | 6/2000 | Reed |
| 6,117,635 | A | 9/2000 | Nazarenko et al. |
| 6,127,121 | A | 10/2000 | Meyer et al. |
| 6,147,199 | A | 11/2000 | Seela et al. |
| 6,248,526 | B1 | 6/2001 | Weimer |
| 6,270,969 | B1 | 8/2001 | Hartley et al. |
| 6,277,608 | B1 | 8/2001 | Hartley et al. |
| 6,280,933 | B1 | 8/2001 | Glazer |
| 6,326,145 | B1 | 12/2001 | Whitcombe |
| 6,329,346 | B1 | 12/2001 | Muhlegger et al. |
| 6,660,845 | B1 | 12/2003 | Gall et al. |
| 6,683,173 | B2 * | 1/2004 | Dempcy et al. ............... 536/25.3 |
| 6,727,356 | B1 | 4/2004 | Reed et al. |
| 6,818,420 | B2 | 11/2004 | Chou et al. |
| 6,964,861 | B1 | 11/2005 | Gerard et al. |
| 6,972,328 | B2 * | 12/2005 | Gall et al. ..................... 536/22.1 |
| 7,019,129 | B1 | 3/2006 | Cook et al. |
| 7,160,997 | B2 | 1/2007 | Chou et al. |
| 7,393,632 | B2 | 7/2008 | Cheo et al. |
| 7,670,823 | B1 | 3/2010 | Hartley et al. |
| 7,754,453 | B2 | 7/2010 | Chou et al. |
| 8,088,583 | B2 | 1/2012 | Chou et al. |
| 2001/0039331 | A1 | 11/2001 | Hunter et al. |
| 2007/0231809 | A1 | 10/2007 | Chou et al. |
| 2009/0081676 | A1 | 3/2009 | Chou et al. |

FOREIGN PATENT DOCUMENTS

| | | |
|---|---|---|
| JP | 200338180 | 2/2003 |
| WO | WO-98/53056 | 11/1998 |
| WO | WO-99/25851 | 5/1999 |
| WO | WO-9951621 | 10/1999 |
| WO | WO-00/41549 | 7/2000 |
| WO | WO-00/75378 | 12/2000 |
| WO | WO-01/42505 | 6/2001 |
| WO | WO-01/64958 | 9/2001 |
| WO | WO-01/86001 | 11/2001 |
| WO | WO-02099141 | 12/2002 |
| WO | WO-03/019143 | 3/2003 |
| WO | WO-03043402 | 5/2003 |
| WO | WO-03/072051 | 9/2003 |

OTHER PUBLICATIONS

U.S. Appl. No. 09/296,281, filed Apr. 22, 1999, Hartley, James L.
U.S. Appl. No. 09/517,466, filed Mar. 2, 2000, Hartley, James et al.
U.S. Appl. No. 09/518,188, filed Mar. 2, 2000, Hartley, James.
EP01115788.0 European Search Report dated Mar. 14, 2006.
EP03711238.0 Office Action dated Mar. 12, 2009.
EP03711238.0 Supplemental European Search Report dated Mar. 14, 2006.
EP03711238.0 Office Action dated Jun. 9, 2008.
EP03711238.0 Office Action dated Jun. 16, 2006.
EP03711238.0 Response to Mar. 12, 2009 Office Action filed Jul. 14, 2009.
EP03711238.0 Response to Jun. 9, 2008 Office Action filed Nov. 20, 2008.
EP03711238.0 Response to Jun. 16, 2006 Office Action filed Jun. 11, 2007.
EP08153863.9 European Search Report dated Jul. 3, 2008.
EP08153863.9 Office Action dated Mar. 26, 2009.
EP08153863.9 Office Action dated Nov. 10, 2008.
EP08153863.9 Response to Mar. 26, 2009 Office Action Filed on Aug. 3, 2009.
EP08153863.9 Response to Nov. 10, 2008 Office action Filed on Mar. 10, 2009.
U.S. Appl. No. 10/087,229 Notice of Allowance dated Jun. 29, 2004.
U.S. Appl. No. 10/087,229 Office Action dated Feb. 13, 2004.
U.S. Appl. No. 10/087,229 Response filed Mar. 26, 2004 to Feb. 13, 2004 Office Action.
U.S. Appl. No. 10/087,229 Terminal Disclaimer filed Jun. 7, 2004.
U.S. Appl. No. 10/222,943 Notice of Allowance dated Jan. 10, 2006.
U.S. Appl. No. 10/222,943 Notice of Allowance dated May 12, 2005.
U.S. Appl. No. 10/222,943 Notice of Allowance dated Jun. 19, 2006.
U.S. Appl. No. 10/222,943 Office Action dated Mar. 31, 2005.
U.S. Appl. No. 10/222,943 Office Action dated May 3, 2004.
U.S. Appl. No. 10/222,943 Office Action dated Jul. 1, 2004.
U.S. Appl. No. 10/222,943 Office Action dated Dec. 27, 2004.
U.S. Appl. No. 10/222,943 Response filed Apr. 25, 2005 to Mar. 31, 2005 Office Action.
U.S. Appl. No. 10/222,943 Response filed Apr. 13, 2005 to Mar. 31, 2005 Office Action.
U.S. Appl. No. 10/222,943 Response filed Jun. 2, 2004 to May 3, 2004 Office Action.
U.S. Appl. No. 10/222,943 Response filed Oct. 1, 2004 to Jul. 1, 2004 Office Action.
U.S. Appl. No. 10/222,943 Response filed Mar. 23, 2005 to Dec. 27, 2004 Office Action.
U.S. Appl. No. 10/222,943 Response filed Jul. 28, 2005 to Notice of Allowance dated May 12, 2005.
U.S. Appl. No. 11/198,924 Office Action dated Feb. 26, 2008.
U.S. Appl. No. 11/198,924 Office Action dated Jul. 10, 2007.
U.S. Appl. No. 11/198,924 Response filed Jan. 10, 2008 to Jul. 10, 2007 Office Action.
U.S. Appl. No. 11/530,915 Office Action dated Feb. 26, 2008.
U.S. Appl. No. 12/197,739 Office Action dated May 22, 2009.
U.S. Appl. No. 12/197,739 Response filed Oct. 19, 2009 to May 22, 2009 Office Action.
U.S. Appl. No. 12/197,739 Notice of Allowance dated Nov. 16, 2009.
JP2003570798 Office Action Dated Dec. 8, 2008.
JP2003570798 Response filed Jun. 5, 2009 to Dec. 8, 2008 Office Action.
JP2003570798 Office Action dated Jul. 29, 2009—untranslated.
U.S. Appl. No. 60/138,376 Provisional Application Expired Jun. 9, 1999.
PCT/US03/05641 International Search dated Oct. 17, 2003.
Barnes, Wayne M. PCR Amplification of up to 35-kb DNA with High Fidelity and High Yield from Bacteriophage Templates. (PNAS) vol. 91, No. 6, 1994, 2216-2220.
Bernad, Antonio, et al. A Conserved 3'-5' Exonuclease Active Site in Prokaryotic and Eukaryotic DNA Polymerases Cell vol. 59, 1989, 219-228.
Braithwaite, Dan K. et al. Compilation, alignment, and phylogenetic relationships of DNA polymerases Nucleic Acids Research vol. 21 (4) 1993, 787-802.
Chou, Quin et al. Use of Dark-Quenched FRET probes in Real-Time PCR American Biotechnology Laboratory vol. 19, No. 8, 2001, 34.
Cline, Janice et al. PCR Fidelity of Pfu DNA Polymerase and Other Thermostable DNA Polymerases Nucleic Acids Research vol. 24, No. 18, Oxford University Press 1996, 3546-3551.
Eckert, Kristin A. et al. High fidelity DNA synthesis by the *Thermus aquaticus* DNA polymerase, Nucleic Acids Research vol. 18, No. 13, 1990, 3739-3744.
Heid, Christian A. et al. Real Time Quantitative PCR Genome Research vol. 6, Cold Spring Harbor Laboratory Press, Woodbury, NY, US 1996, 986-994.
Holland, Pamela M. et al. Detection of Specific Polymerase Chain Reaction Product by Utilizing the 5'->3' Exonuclease Activity of *Thermus aquaticus* DNA Polymerase, (PNAS) vol. 88, National Academy of Sciences of the USA 1991, 7276-7280.

(56) References Cited

OTHER PUBLICATIONS

Keohavong, Phouthone et al. Fidelity of DNA polymerases in DNA amplification, (PNAS) 86 1989, 9253-9257.
Kreuzer, Karl-Anton et al. Simultaneous Absolute Quantification of Target and Control Templates by Real-Time Fluorescence Reverse Transcription-PCR Using 4-(4'-Dimethylaminophenylazo) Benzoic Acid as a Dark Quencher Dye, Clinical Chemistry vol. 47, No. 3, 2001, 486-490.
Kunkel, T. A. et al. On the Fidelity of DNA Synthesis, J. Biol. Chem vol. 261 1986, 13610-13616.
Lee, Linda G. et al. Allelic Discrimination by Nick-Translation PCR With Fluorogenic Probes, Nucleic Acids Research vol. 21, No. 16, Oxford University Press 1993, 3761-3766.
Lundberg, Kelly S. et al. High-fidelity amplification using a thermostabile DNA polymerase isolated from *Pyrococcus furiosus* Gene, vol. 108 1991, 1-6.
Nazarenko, Irina A. et al. A Closed Tube Format for Amplification and Detection of DNA Based on Energy Transfer, Nucleic Acids Research vol. 25, No. 12, Oxford University Press, Oxford, England 1997, 2516-2521.
Perler, Francine et al. Intervening Sequences in an Archaea DNA Polymerase Gene, (PNAS) 89 1992, 5577-5581.
Perrino, Fred et al. Hydrolysis of 3'-terminal mispairs in vitro by the 3'-5' exonuclease of DNA polymerase delta permits subsequent extension by DNA polymerase alpha. Biochemistry vol. 29, 1990, 5226-5231.
Ranasinghe, et al. Linear fluorescent oligonucleotide probes with a acridine quencher generate a signal upon hybridision, Chem Commun. 2001, 1480-1481.
Reyland, Mary et al. Specificity of proofreading by the 3'-5' exonuclease of the DNA polymerase-primase of Drosophila melanogaster, The Journal of Biological Chemistry vol. 263, 1988, 6518-6524.
Saiki, Randall K. et al. Enzymatic Amplification of Beta-Globin Genomic Sequences and Restriction Site Analysis for Diagnosis of Sickle Cell Anemia. Science vol. 230, 1985, 1350-1354.
Saiki, Randall K. et al. Primer-Directed Enzymatic Amplification of DNA with a Thermostable DNA Polymerase Science, vol. 239, 1988, 487-491.
Taquet, et al. Calorimetric investigation of ethidium and netropsin binding to chicken erythrocyte chromatin. Biochemistry vol. 37, 1998, 9119-26.
Tindall, et al. Fidelity of DNA Synthesis by the *Thermus aquaticus* DNA Polymerase, Biochemistry, vol. 27, 1998, pp. 6008-6013.
Tyagi, Sanjay et al. Molecular Beacons: Probes that Fluoresceupon Hybridization Nature Biotechnology, vol. 14, 1996, 303-308.
Whitcombe, D. et al. Detection of PCR products using self probing amplicons and fluorescence Nat. Biotechnol. 17(8): Nature Publishing Group 1999, 804-807.
Asseline, et al., *Bioconjugate Chem.*, vol. 7, 1996, 369-379.
Boidot-Forget, et al., "Site-Specific Cleavage of Single-Stranded and Double Stranded DNA Sequences by Oligodeoxyribonucleosides Covalently Linked to an lintercalating Agent and an EDTA-Fe Chelate", *Gene*, vol. 72, 1998, 361-371.
Cazenave, et al., *Nucleic Acid Research*, vol. 15, No. 24, 1987, 10507-10521.
Dearing, et al., *Nucleic Acids Research*, vol. 9, No. 6, 1981, 1483-1497.
Gamper, H. B., "Facile Preparation of Nuclease Resistant 3' Modified Ollcodeoxvnucleotides", *Nucl. Acids Res.*: vol. 21, 1993, 145-150.
Goodchild, John, "Conjugates of Oligonucleotides and Modified Oligonucleotides: A Review of Their Synthesis and Properties", *Bioconjugate Chemistry*, vol. 1, No. 3, American Chemical Society, 1990, 165-187.
Hinrichsen, et al., *PNAS*, vol. 89, 1992, 8601-8605.
Kutyavin, I. et al., "3'-Minor groove binder-DNA probes increase sequence specificity at PCR extension temperatures", *Nucleic Acids Research*, vol. 28, No. 2, 2000, pp. 655-661.
Shaw, et al., *Nucleic Acids Research*, vol. 19, No. 4, 1996, 747-750.
Shinozuka, et al., *J. Chem. Soc. Chem. Commun.*, 1994, 1377-1378.
Sun, et al., *PNAS*, vol. 86, 1989, 9198-9202.
Thuong, N. T. "Oligo(Alpha-Deosynucleotide)s Covalently Linked to Intercalating Agents: Differential Binding to Ribo- and Deoxyribopolynucleotides and Stability Towards Nuclease Digestion", *Proc Nat Acad Sci USA*, 84, Aug. 1987, 5129-5133.
Verspieren, et al., "An Acridine-Linked Oligodeoxynucleotide Targeted to the", *Gene*, vol. 61, 1987, 307-315.
Asseline, et al., "Nucleic acid-binding molecules with high affinity and base sequence specificity: Intercalating agents covalently linked to oligodeoxynucleotides", *Proc. Natl. Acad. Sci.*, vol. 81, 1984, 3297-3301.
Asseline, et al., "Oligodeoxynucleotides Covalently Linked to Intercalating Dyes as Base Sequence-Specific Ligands; Influence of Dye Attachment Site", *EMBO Journal*, vol. 3(4), 1984, 795-800.
Asseline, et al., "Synthesis and properties of oligonucleotides covalently linked to intercalating agents", *New J. Chem*, vol. 21, 1997, 5-17.
Extract from Glen Research Product Catalog, 2013, 1 Page.
Helene, C., "Artificial control of gene expression by oligodeoxynucleotides covalently linked to intercalating agents", *Br. J. Cancer*, vol. 60, 1989, 157-160.
Lancelot et al., "Proton and Phosphorus Nuclear Magnetic Resonance Studies of an Oligothymidylate Covalently Linked to an Acridine Derivative and of Its Binding to Complementary Sequences", *Biochemistry*, vol. 24, 1985, 2521-2529.
Nelson, et al., "Oligonucleotide labeling methods. 3. Direct iabeling of oligonucleotides employing a novel, non-nucJeosidic, 2-aminobulvl-1,3-orooanedioJ backbone", *Nucl. Acids. Res.*; vol. 20, 1992, 6253-6259.
Ranasinghe, Rohan et al., "Linear fluorescent oligonucleotide probes with an acridine quencher generate a signal upon hybridisation", *Chem. Commun.*, 2001, 1480-1481.
Toulme, et al., "Specific inhibition of mRNA translation by complementary oligonucleotides covalently linked to intercalating agents", *Proc. Natl. Acad. Sci. USA*, vol. 83, 1986, 1227-1231.

* cited by examiner

BCL-P4 Probe (FAM/TAMRA):
Real Time PCR using Taq + Pwo DNA Polymerase

BCL-P4 Probe (FAM/TAMRA):
Real Time PCR using Taq + Pwo DNA Polymerase

Multicomponent analysis of FAM/TAMRA FET Oligo Primers (ABCG-P2):
Primers itself Multicomponent analysis of FAM/TAMRA FET Oligo Primers (ABCG-P2):
Primers itself Multicomponent analysis of FAM/TAMRA FET Oligo Primers (ABCG-P2):
Primers + Template Multicomponent analysis of FAM/TAMRA FET Oligo Primers (ABCG-P2):
Primers + Template Multicomponent analysis of FAM/BHQ1 FET Oligo Primers (ABCG-P1):
Primers itself Multicomponent analysis of FAM/BHQ1 FET Oligo Primers (ABCG-P1):
Primers itself Multicomponent analysis of FAM/BHQ1 FET Oligo Primers (ABCG-P1):
Primers + Template Multicomponent analysis of FAM/BHQ1 FET Oligo Primers (ABCG-P1):
Primers + Template

SEQUENCE LISTING

```
<160> NUMBER OF SEQ ID NOS: 25

<210> SEQ ID NO 1
<211> LENGTH: 21
<212> TYPE: DNA
<213> ORGANISM: human

<400> SEQUENCE: 1
ggtggtggag gagctcttca g                                              21

<210> SEQ ID NO 2
<211> LENGTH: 20
<212> TYPE: DNA
<213> ORGANISM: human

<400> SEQUENCE: 2
ccagcctccg ttatcctgga                                                20

<210> SEQ ID NO 3
<211> LENGTH: 27
<212> TYPE: DNA
<213> ORGANISM: human

<400> SEQUENCE: 3
cctgtggatg actgagtacc tgaaccg                                        27

<210> SEQ ID NO 4
<211> LENGTH: 27
<212> TYPE: DNA
<213> ORGANISM: human
```

<400> SEQUENCE: 4
cctgtggatg actgagtacc tgaaccg                                              27

<210> SEQ ID NO 5
<211> LENGTH: 27
<212> TYPE: DNA
<213> ORGANISM: human

<400> SEQUENCE: 5
cctgtggatg actgagtacc tgaaccg                                              27

<210> SEQ ID NO 6
<211> LENGTH: 27
<212> TYPE: DNA
<213> ORGANISM: human

<400> SEQUENCE: 6
cctgtggatg actgagtacc tgaaccg                                              27

<210> SEQ ID NO 7
<211> LENGTH: 27
<212> TYPE: DNA
<213> ORGANISM: human

<400> SEQUENCE: 7
cctgtggatg actgagtacc tgaaccg                                              27

<210> SEQ ID NO 8
<211> LENGTH: 19
<212> TYPE: DNA
<213> ORGANISM: human

<400> SEQUENCE: 8
gagctacgag ctgcctgac                                                       19

<210> SEQ ID NO 9
<211> LENGTH: 18
<212> TYPE: DNA
<213> ORGANISM: human

<400> SEQUENCE: 9
gactccatgc ccaggaag                                                        18

<210> SEQ ID NO 10
<211> LENGTH: 21
<212> TYPE: DNA
<213> ORGANISM: human

<400> SEQUENCE: 10
catcaccatt ggcaatgagc g                                                    21

<210> SEQ ID NO 11
<211> LENGTH: 21
<212> TYPE: DNA
<213> ORGANISM: human

<400> SEQUENCE: 11
catcaccatt ggcaatgagc g                                                    21

<210> SEQ ID NO 12
<211> LENGTH: 21
<212> TYPE: DNA

```
<213> ORGANISM: human

<400> SEQUENCE: 12
catcaccatt ggcaatgagc g                                              21

<210> SEQ ID NO 13
<211> LENGTH: 21
<212> TYPE: DNA
<213> ORGANISM: human

<400> SEQUENCE: 13
catcaccatt ggcaatgagc g                                              21

<210> SEQ ID NO 14
<211> LENGTH: 21
<212> TYPE: DNA
<213> ORGANISM: human

<400> SEQUENCE: 14
catcaccatt ggcaatgagc g                                              21

<210> SEQ ID NO 15
<211> LENGTH: 23
<212> TYPE: DNA
<213> ORGANISM: human

<400> SEQUENCE: 15
cccaaaaatt cattatgctg caa                                            23

<210> SEQ ID NO 16
<211> LENGTH: 27
<212> TYPE: DNA
<213> ORGANISM: human

<400> SEQUENCE: 16
cagcattcca cgatatggat ttacggc                                        27

<210> SEQ ID NO 17
<211> LENGTH: 27
<212> TYPE: DNA
<213> ORGANISM: human

<400> SEQUENCE: 17
cagcattcca cgatatggat ttacggc                                        27

<210> SEQ ID NO 18
<211> LENGTH: 58
<212> TYPE: DNA
<213> ORGANISM: human

<400> SEQUENCE: 18
atcagcattc cacgatatgg atttacggca tcagttgcag cataatgaat ttttggga      58

<210> SEQ ID NO 19
<211> LENGTH: 23
<212> TYPE: DNA
<213> ORGANISM: human

<400> SEQUENCE: 19
ggaagaatgt gtcagcctca aag                                            23

<210> SEQ ID NO 20
<211> LENGTH: 23
```

```
<212> TYPE: DNA
<213> ORGANISM: human

<400> SEQUENCE: 20
ctgacctgaa gcacttgaag gag                                            23

<210> SEQ ID NO 21
<211> LENGTH: 17
<212> TYPE: DNA
<213> ORGANISM: human

<400> SEQUENCE: 21
tgaaatcggc tcccgca                                                   17

<210> SEQ ID NO 22
<211> LENGTH: 19
<212> TYPE: DNA
<213> ORGANISM: human

<400> SEQUENCE: 22
tgaaatcgac tcccgcaga                                                 19

<210> SEQ ID NO 23
<211> LENGTH: 16
<212> TYPE: DNA
<213> ORGANISM: human

<400> SEQUENCE: 23
tgaaatcggc tcccgc                                                    16

<210> SEQ ID NO 24
<211> LENGTH: 16
<212> TYPE: DNA
<213> ORGANISM: human

<400> SEQUENCE: 24
tgaaatcggc tcccgc                                                    16

<210> SEQ ID NO 25
<211> LENGTH: 18
<212> TYPE: DNA
<213> ORGANISM: human

<400> SEQUENCE: 25
tgaaatcgac tcccgcag                                                  18
```

METHODS OF USING FET LABELED OLIGONUCLEOTIDES THAT INCLUDE A 3'-5' EXONUCLEASE RESISTANT QUENCHER DOMAIN AND COMPOSITIONS FOR PRACTICING THE SAME

CROSS-REFERENCE TO RELATED APPLICATIONS

This application claims priority from and is a continuation of U.S. Application Ser. No. 12/786,194 filed 24 May 2010; which is a continuation application of U.S. application Ser. No. 12/197,739 filed 25 Aug. 2008, now U.S. Pat. No. 7,754,453; which is a continuation of U.S. application Ser. No. 11/530,915 filed 12 Sep. 2006, abandoned; which is a continuation of U.S. application Ser. No. 11/198,924, filed 4 Aug. 2005, abandoned; which is a continuation of U.S. application Ser. No. 10/222,943, filed 15 Aug. 2002, now U.S. Pat. No. 7,160,997; which is a continuation-in-part of U.S. application Ser. No. 10/087,229, filed 27 Feb. 2002, now U.S. Pat. No. 6,818,420, the disclosures of all of which are incorporated herewith in their entireties.

INTRODUCTION

1. Technical Field

The technical field of this invention is the polymerase chain reaction (PCR); and particularly high fidelity real-time PCR.

2. Background of the Invention

The polymerase chain reaction (PCR) is a powerful method for the rapid and exponential, amplification of target nucleic acid sequences. PCR has facilitated the development of gene characterization and molecular cloning technologies including the direct sequencing of PCR amplified DNA, the determination of allelic variation, and the detection of infectious and genetic disease disorders. PCR is performed by repeated cycles of heat denaturation of a DNA template containing the target sequence, annealing of opposing primers to the complementary DNA strands, and extension of the annealed primers with a DNA polymerase. Multiple PCR cycles result in the exponential amplification of the nucleotide sequence delineated by the flanking amplification primers.

An important modification of the original PCR technique was the substitution of *Thermus aquaticus* (Taq) DNA polymerase in place of the Klenow fragment of *E. coli* DNA pol I (Saiki, et al. Science, 230:1350-1354 (1988)). The incorporation of a thermostable DNA polymerase into the PCR protocol obviates the need for repeated enzyme additions and permits elevated annealing and primer extension temperatures which enhance the specificity of primer:template associations. Taq DNA polymerase thus serves to increase the specificity and simplicity of PCR.

Although Taq DNA polymerase is used in the vast majority of PCR performed today, it has a fundamental drawback: purified Taq DNA polymerase enzyme is devoid of 3' to 5' exonuclease activity and thus cannot excise misinserted nucleotides (Tindall, et al., Biochemistry, 29:5226-5231 (1990)). Consistent with these findings, the observed error rate (mutations per nucleotide per cycle) of Taq polymerase is relatively high; estimates range from $2\times10^{-4}$ during PCR (Saiki et al., Science, 239:487-491 (1988); Keohavaong et al. Proc. Natl. Acad. Sci. USA, 86:9253-9257 (1989)) to $2\times10^{-5}$ for base substitution errors produced during a single round of DNA synthesis of the lacZ gene (Eckert et al., Nucl. Acids Res. 18:3739-3744 (1990)).

Polymerase induced mutations incurred during PCR increase arithmetically as a function of cycle number. For example, if an average of two mutations occur during one cycle of amplification, 20 mutations will occur after 10 cycles and 40 will occur after 20 cycles. Each mutant and wild type template DNA molecule will be amplified exponentially during PCR and thus a large percentage of the resulting amplification products will contain mutations. Mutations introduced by Taq DNA polymerase during DNA amplification have hindered PCR applications that require high fidelity DNA synthesis. Several independent studies suggest that 3' to 5' exonuclease-dependent proofreading enhances the fidelity of DNA synthesis (Reyland et al, J. Biol. Chem., 263:6518-6524, 1988; Kunkel et al, J. Biol. Chem., 261:13610-13616, 1986; Bernad et al, Cell, 58:219-228, 1989). As such, it is desirable, where possible, to include a 3' to 5' exonuclease-dependent proofreading activity in PCR based reactions. For example, If Taq DNA Polymerase (error rate $2\times10^{-4}$) is used to amplify a 100 bp sequence for 40 cycles by PCR, about 55% of the amplification products will contain one or more errors. In contrast, if a Pwo DNA Polymerase having proof-reading activities is used for the amplification, only 10% of the products will contain an error under the same conditions. The error rate produced by a mixture of Taq DNA Polymerase and a proofreading DNA Polymerase between these two values (Cline et al, Nucleic Acids Res., 24(18):3546-51, 1996).

In many PCR based reactions, a signal producing system is employed, e.g., to detect the production of amplified product. One type of signal producing system that is attractive for use in PCR based reactions is the fluorescence energy transfer (FET) system, in which a nucleic acid detector includes fluorescence donor and acceptor groups. FET label systems include a number of advantages over other labeling systems, including the ability to perform homogeneous assays in which a separation step of bound vs. unbound labeled nucleic acid detector is not required.

In such real time detection systems using a FET labeled nucleic acid detector, high fidelity amplification is critical. Any error in sequences where a FET labeled nucleic acid detector binds can cause probes not to bind or wrong probes to bind in the case of allele discrimination, resulting in weak signal or the wrong signal being produced. For example, if a 30 bp PCR fragment which is the target of a FET labeled probe is amplified using Taq DNA Polymerase for 40 cycles, about 22% of the amplification fragments will contain one or more errors. In contrast. if a Pwo DNA Polymerase having proof-reading activities is used for the amplification, only 3% of the amplification fragments will contain an error under the same conditions. Therefore. the standard low fidelity amplification can cause a decrease in sensitivity or mis-typing in the case of allele discrimination.

However, as discovered by the current invention a disadvantage of currently available FET labeled nucleic acids having TAMRA or Dabcyl as a quencher is that such nucleic acids are subject to 3'→5' exonuclease degradation. Accordingly, such FET labeled nucleic acids are not suitable for use in high fidelity PCR applications, where 3'→5' exonuclease activity, i.e., proofreading activity, is present.

As such, there is significant interest in the identification and development of FET labeled nucleic acids that can be used in high fidelity PCR applications.

RELEVANT LITERATURE

U.S. patents of interest include: U.S. Pat. Nos. 5,538,848 and 6,248,526. Also of interest are: WO 01/86001 and WO 01/42505.

SUMMARY OF THE INVENTION

Methods and compositions are provided for detecting a primer extension product in a reaction mixture. In certain embodiments of the subject methods, a primer extension reaction is conducted in the presence of a polymerase having exonuclease activity and at least one FET labeled oligonucleotide probe that includes a 3'→5' exonuclease resistant quencher domain. In certain embodiments a nucleic acid intercalator is covalently bonded to the FET labeled oligonucleotide. In certain embodiments, a minor groove binder is employed in the reaction. In these latter two embodiments, the polymerase may or may not include a 3'→5' exonuclease activity. Also provided are systems and kits for practicing the subject methods. The subject invention finds use in a variety of different applications, and is particularly suited for use in high fidelity PCR based reactions, including SNP detection applications. allelic variation detection applications, and the like.

DEFINITIONS

As used herein, "nucleic acid" means either DNA, RNA, single-stranded or double-stranded, and any chemical modifications thereof. Modifications include, but are not limited to, those which provide other chemical groups that incorporate additional charge, polarizability, hydrogen bonding, electrostatic interaction, and functionality to the nucleic acid. Such modifications include, but are not limited to, 2'-position sugar modifications, 5-position pyrimidine modifications, 8-position purine modifications, modifications at exocyclic amines, substitution of 4-thiouridine, substitution of 5-bromo or 5-iodo-uracil; backbone modifications, methylations, unusual base-pairing combinations such as the isobases isocytidine and isoguanidine and the like. Modifications can also include 3' and 5' modifications such as capping.

As used herein, "fluorescent group" refers to a molecule that, when excited with light having a selected wavelength, emits light of a different wavelength. Fluorescent groups may also be referred to as "fluorophores".

As used herein, "fluorescence-modifying group" refers to a molecule that can alter in any way the fluorescence emission from a fluorescent group. A fluorescence-modifying group generally accomplishes this through an energy transfer mechanism. Depending on the identity of the fluorescence-modifying group, the fluorescence emission can undergo a number of alterations, including, but not limited to, attenuation, complete quenching, enhancement, a shift in wavelength, a shift in polarity, a change in fluorescence lifetime. One example of a fluorescence-modifying group is a quenching group.

As used herein, "energy transfer" refers to the process by which the fluorescence emission of a fluorescent group is altered by a fluorescence-modifying group. If the fluorescence-modifying group is a quenching group, then the fluorescence emission from the fluorescent group is attenuated (quenched). Energy transfer can occur through fluorescence resonance energy transfer, or through direct energy transfer. The exact energy transfer mechanisms in these two cases are different. It is to be understood that any reference to energy transfer in the instant application encompasses all of these mechanistically-distinct phenomena. Energy transfer is also referred to herein as fluorescent energy transfer or FET.

As used herein, "energy transfer pair" refers to any two, molecules that participate in energy transfer. Typically, one of the molecules acts as a fluorescent group, and the other acts as a fluorescence-modifying group. The preferred energy transfer pair of the instant invention comprises a fluorescent group and a quenching group. In some cases, the distinction between the fluorescent group and the fluorescence-modifying group may be blurred. For example, under certain circumstances, two adjacent fluorescein groups can quench one another's fluorescence emission via direct energy transfer. For this reason, there is no limitation on the identity of the individual members of the energy transfer pair in this application. All that is required is that the spectroscopic properties of the energy transfer pair as a whole change in some measurable way if the distance between the individual members is altered by some critical amount.

"Energy transfer pair" is used to refer to a group of molecules that form a single complex within which energy transfer occurs. Such complexes may comprise, for example, two fluorescent groups which may be different from one another and one quenching group, two quenching groups and one fluorescent group, or multiple fluorescent groups and multiple quenching groups. In cases where there are multiple fluorescent groups and/or multiple quenching groups, the individual groups may be different from one another.

As used herein, "quenching group" refers to any fluorescence-modifying group that can attenuate at least partly the light emitted by a fluorescent group. We refer herein to this attenuation as "quenching". Hence, illumination of the fluorescent group in the presence of the quenching group leads to an emission signal that is less intense than expected, or even completely absent. Quenching occurs through energy transfer between the fluorescent group and the quenching group.

As used herein, "fluorescence resonance energy transfer" or "FRET" refers to an energy transfer phenomenon in which the light emitted by the excited fluorescent group is absorbed at least partially by a fluorescence-modifying group. If the fluorescence-modifying group is a quenching group, then that group can either radiate the absorbed light as light of a different wavelength, or it can dissipate it as heat. FRET depends on an overlap between the emission spectrum of the fluorescent group and the absorption spectrum of the quenching group. FRET also depends on the distance between the quenching group and the fluorescent group. Above a certain critical distance, the quenching group is unable to absorb the light emitted by the fluorescent group, or can do so only poorly.

As used herein "direct energy transfer" refers to an energy transfer mechanism in which passage of a photon between the fluorescent group and the fluorescence-modifying group does not occur. Without being bound by a single mechanism, it is believed that in direct energy transfer, the fluorescent group and the fluorescence-modifying group interfere with each others electronic structure. If the fluorescence-modifying group is a quenching group, this will result in the quenching group preventing the fluorescent group from even emitting light.

In general, quenching by direct energy transfer is more efficient than quenching by FRET. Indeed, some quenching groups that do not quench particular fluorescent groups by FRET (because they do not have the necessary spectral overlap with the fluorescent group) can do so efficiently by direct energy transfer. Furthermore, some fluorescent groups can act as quenching groups themselves if they are close enough to other fluorescent groups to cause direct energy transfer. For example, under these conditions, two adjacent fluorescein groups can quench one another's fluorescence effectively. For these reasons, there is no limitation on the nature of the fluorescent groups and quenching groups useful for the practice of this invention.

An example of "stringent hybridization conditions" is hybridization at 50° C. or higher and 6.0×SSC (900 mM NaCl/90 mM sodium citrate). Another example of stringent hybridization conditions is overnight incubation at 42° C. or higher in a solution: 50% formamide, 6×SSC (900 mM NaCl, 90 mM trisodium citrate), 50 mM sodium phosphate (pH7.6), 10% dextran sulfate, and 20 µg/ml denatured, sheared salmon sperm DNA. Stringent hybridization conditions are hybridization conditions that are at least as stringent as the above representative conditions, where conditions are considered to be at least as stringent if they are at least about 80% as stringent, typically at least about 90% as stringent as the above specific stringent conditions. Other stringent hybridization conditions are known in the art and may also be employed.

As used herein, the term "nucleic acid intercalator" refers to a molecule that binds to a nucleic acid by inserting itself in between base pairs of adjacent nucleotides without unwinding and without extension of the nucleic acid helix. In general, nucleic acid intercalators are aromatic compounds having a flat configuration, and are preferably polycyclic.

As used herein, the term "minor groove binder" refers to a molecule that binds to a nucleic acid by inserting itself into the minor groove of a DNA helix. In general, minor groove binders are capable of binding within the minor groove of a DNA helix with an association constant of $10^3 M^{-1}$ or greater. In addition, minor groove binders generally have crescent shaped three-dimensional structures.

As used herein, "3' end" means at any location on the oligonucleotide from and including the 3' terminus to the center of the oligonucleotide, usually at any location from and including the 3' terminus to about 10 bp from the 3' terminus, and more usually at any location from and including the 3' terminus to about 5 bp from the 3' terminus.

As used herein, "5' end" means at any location on the oligonucleotide from and including the 5' terminus to the center of the oligonucleotide, usually at any location from and including the 5' terminus to about 10 bp from the 5' terminus, and more usually at any location from and including the 5' terminus to about 5 bp from the 5' terminus.

DESCRIPTION OF THE SPECIFIC EMBODIMENTS

Figures 1, 1A:
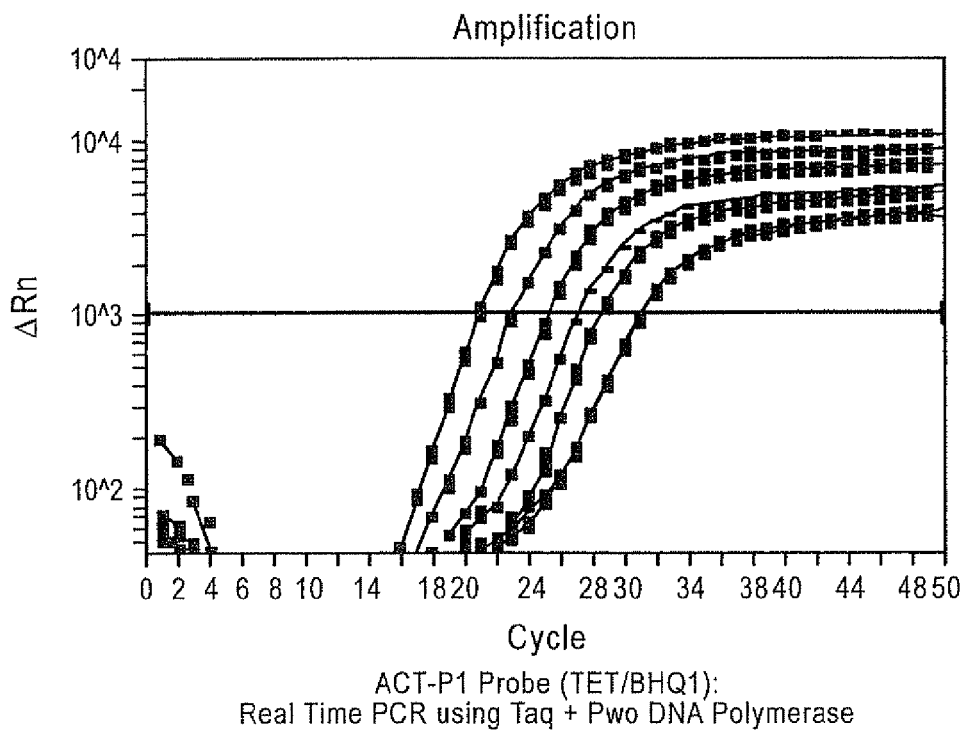
FIGS. 1A to 1E provide graphical results of assays comparing the function of various TET labeled FET probes under high fidelity and standard PCR conditions.
Figures 1, 1A, 2:
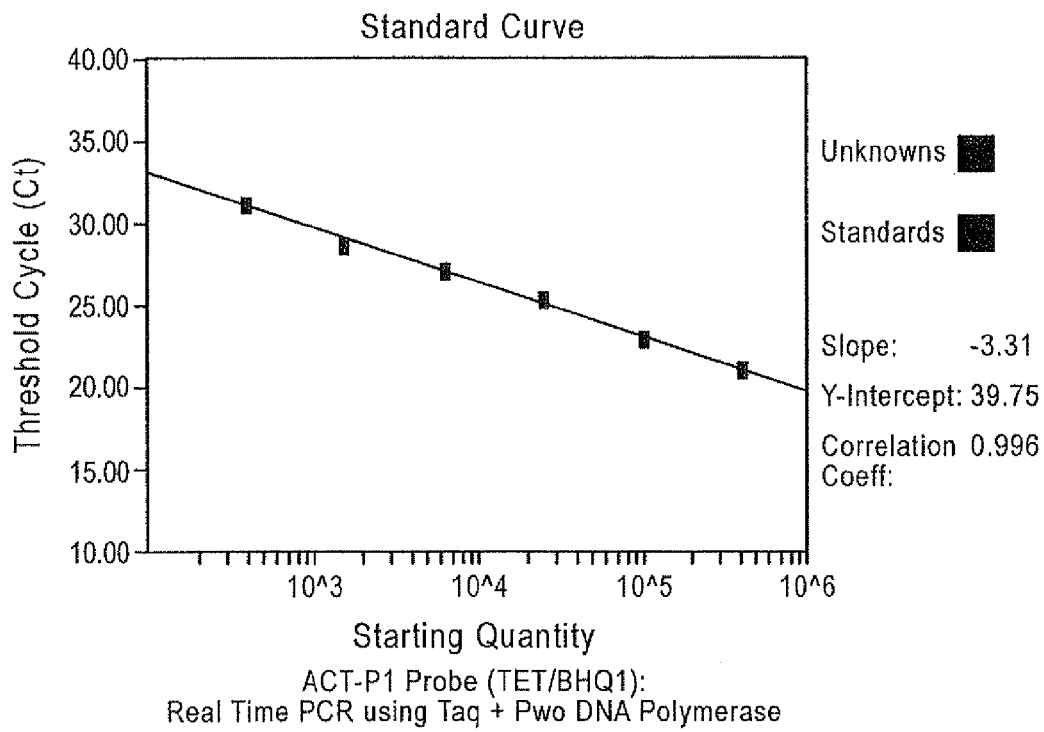

Methods and compositions are provided for detecting a primer extension product in a reaction mixture. In certain embodiments of subject methods, a primer extension reaction is conducted in the presence of a polymerase having 3'→5' exonuclease activity and at least one FET labeled oligonucleotide probe that includes a 3'→5' exonuclease resistant quencher domain. In certain embodiments, a nucleic acid intercalator covalently bonded to said FET labeled oligonucleotide. In certain embodiments, a minor groove binder is employed in the reaction. In these latter two embodiments, the polymerase employed may or may not have 3'→5' exonuclease activity. Also provided are systems and kits for practicing the subject methods. The subject invention finds use in a variety of different applications, and is particularly suited for use in high fidelity PCR based reactions, including SNP detection applications, allelic variation detection applications, and the like.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms "a," "an" and "the" include plural reference unless the context clearly dictates otherwise. Unless defined otherwise, all technical and scientific terms used herein have the same meaning as commonly understood to one of ordinary skill in the art to which this invention belongs.

Where a range of values is provided, it is understood that each intervening value, to the tenth of the unit of the lower limit unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing those components that are described in the publications that might be used in connection with the presently described invention.

As summarized above, the subject invention provides methods of detecting the production of a primer extension product in a primer extension reaction mixture by using a FET labeled oligonucleotide probe. In further describing the subject invention, the methods are described first in greater detail, followed by a review of representative specific applications, in which the methods finds use, as well as systems and kits, that find use in practicing the subject methods.

Methods

As summarized above, the subject invention provides methods for detecting the production of primer extension products in a primer extension reaction mixture. In other words, the subject invention provides methods of determining whether primer extension products are produced in a primer extension reaction. By primer extension product is meant a nucleic acid molecule that results from a template dependent primer extension reaction. Template dependent primer extension reactions are those reactions in which a polymerase extends a nucleic acid primer molecule that is hybridized to a template nucleic acid molecule, where the sequence of bases that is added to the terminus of the primer nucleic acid molecule is determined by the sequence of bases in the template strand. Template dependent primer extension reactions include both amplification and non-amplification primer extension reactions. In many embodiments of the subject invention, the template dependent primer extension reaction in which the production of primer extension products is detected is an amplification reaction, e.g., a polymerase chain reaction (PCR).

A feature of certain embodiments of the subject methods is that the template dependent primer extension reaction in which the production of primer extension products is detected is a "high fidelity" reaction. By "high fidelity" reaction is meant that the reaction has a low error rate, i.e., a low rate of wrong nucleotide incorporation. As such, the error rate of the subject reactions is typically less than about $2 \times 10^{-4}$, usually less than about $1 \times 10^{-5}$ and more usually less than about $1 \times 10^{-6}$. In other embodiments, the reaction mixture is not a high fidelity reaction mixture.

Preparation of High Fidelity Reaction Mixture

In practicing the subject methods of these embodiments, the first step is to produce a "high fidelity" primer extension mixture, e.g., a composition of matter that includes all of the elements necessary for a high fidelity primer extension reaction to occur, where the primer extension mixture further includes at least one FET labeled oligonucleotide that includes a 3'→5' exonuclease resistant quencher domain.

FET occurs when a suitable fluorescent energy donor and an energy acceptor moiety are in close proximity to one another. The excitation energy absorbed by the donor is transferred to the acceptor which can then further dissipate this energy either by fluorescent emission if a fluorophore, or by non-fluorescent means if a quencher. A donor-acceptor pair comprises two fluorophores having overlapping spectra, where the donor emission overlaps the acceptor absorption, so that there is energy transfer from the excited fluorophore to the other member of the pair. It is not essential that the excited fluorophore actually fluoresce, it being sufficient that the excited fluorophore be able to efficiently absorb the excitation energy and efficiently transfer it to the emitting fluorophore.

As such, the FET labeled oligonucleotides employed in the subject methods are nucleic acid detectors that include a fluorophore domain where the fluorescent energy donor, i.e., donor, is positioned and an acceptor domain where the fluorescent energy acceptor, i.e., acceptor, is positioned. As mentioned above, the donor domain includes the donor fluorophore. The donor fluorophore may be positioned anywhere in the nucleic acid detector, but is typically present at the 5' terminus of the detector.

The acceptor domain includes the fluorescence energy acceptor. The acceptor may be positioned anywhere in the acceptor domain, but is typically present at the 3' terminus of the nucleic acid detector.

In addition to the fluorophore and acceptor domains, the FET labeled oligonucleotides also include a target nucleic acid binding domain, which binds to a target nucleic acid sequence, e.g., under stringent hybridization conditions (as defined above). This target binding domain typically ranges in length from about 10 to about 60 nt, usually from about 15 to about 30 nt. Depending on the nature of the oligonucleotide and the assay itself, the target binding domain may hybridize to a region of the template nucleic acid or a region of the primer extension product. For example, where the assay is a 5' nuclease assay, e.g., in which a Taqman type oligonucleotide probe is employed, the target binding domain hybridizes under stringent conditions to a target binding site of the template nucleic acid, which is downstream or 3' of the primer binding site. In alternative embodiments, e.g., in molecular beacon type assays, the target binding domain hybridizes to a domain of a primer extension product.

The overall length of the FET labeled oligonucleotides, which includes all three domains mentioned above, typically ranges from about 10 to about 60 nt, usually from about 15 to about 30 nt.

The donor fluorophore of the subject probes is typically one that is excited efficiently by a single light source of narrow bandwidth, particularly a laser source. The emitting or accepting fluorophores are selected to be able to receive the energy from the donor fluorophore and emit light. Usually the donor fluorophores will absorb in the range of about 350-800 nm, more usually in the range of about 350-600 nm or 500-750 nm. The transfer of the optical excitation from the donor to the acceptor depends on the distance between the two fluorophores. Thus, the distance must be chosen to provide efficient energy transfer from the donor to the acceptor. The distance between the donor and acceptor moieties on the FET oligonucleotides employed in the subject invention, at least in certain configurations (such as upon intramolecular association) typically ranges from about 10 to about 100 angstroms The fluorophores for FET pairs may be selected so as to be from a similar chemical family or a different one, such as cyanine dyes, xanthenes or the like. Fluorophores of interest include, but are not limited to: fluorescein dyes (e.g., 5-carboxyfluorescein (5-FAM), 6-carboxyfluorescein (6-FAM), 2',4',1,4tetrachlorofluorescein (TET), 2',4',5',7',1,4-hexachlorofluorescein (HEX), and 2',7'-dimethoxy-4',5'-dichloro-6-carboxyfluorescein (JOE)), cyanine dyes such as Cy5, dansyl derivatives, rhodamine dyes (e.g., tetramethyl-6-carboxyrhodamine (TAMRA), and tetrapropano-6-carboxyrhodamine (ROX)), DABSYL, DABCYL, cyanine, such as Cy3, anthraquinone, nitrothiazole, and nitroimidazole compounds, and the like. Fluorophores of interest are further described in WO 01/42505 and WO 01/86001, as well as the priority U.S. applications of these documents, the disclosures of the latter of which are herein incorporated by reference.

A feature of the subject FET labeled oligonucleotides is that they are 3'→5' exonuclease resistant. As such, they are not degraded by exonucleases, i.e., enzymes having 3'→5' exonuclease activity. The 3'→5' exonuclease resistance of the subject FET labeled oligonucleotides may arise from the presence of the acceptor moiety present in the acceptor domain of the FET labeled oligonucleotide. In many, though not all embodiments, the acceptor moiety is present at the 3' terminus of the acceptor domain, and in many embodiments at the 3' terminus of the FET labeled oligonucleotide as a whole.

Any acceptor or donor that imparts 3'→5' exonuclease resistance onto the FET labeled oligonucleotides may be employed. In many embodiments, the acceptor moiety is a quencher molecule, e.g., a molecule that absorbs transferred energy but does not emit fluorescence, e.g., a dark quencher. In many embodiments, the dark quencher has maximum absorbance of between about 400 and about 700 nm, and often between about 500 and about 600 nm.

In certain embodiments, the dark quencher comprises a substituted 4-(phenyldiazenyl)phenylamine structure, often comprising at least two residues selected from aryl, substituted aryl, heteroaryl, substituted heteroaryl and combination thereof, wherein at least two of said residues are covalently linked via an exocyclic diazo bond.

In certain embodiments, the dark quencher is described by the following formula:

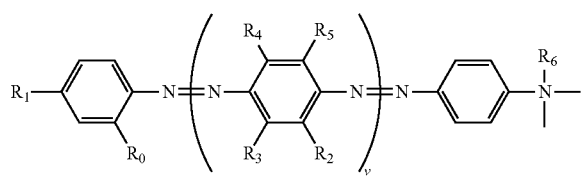

wherein:

$R_0$, $R_1$, $R_2$, $R_3$, $R_4$, $R_5$ are independently: —H, halogen, —O(CH$_2$)$_n$CH$_3$, —(CH$_2$)$_n$CH$_3$, —NO$_2$, SO$_3$, —N[(CH$_2$)$_n$CH$_3$]$_2$ wherein n=0 to 5 or —CN;

$R_6$ is —H or —(CH$_2$)$_n$CH$_3$ where n=0 to 5; and v is a number from 0 to 10.

Dark quenchers of interest are further described in WO 01/42505 and WO 01/86001, as well as the priority U.S. Applications of these documents, the disclosures of the latter of which are herein incorporated by reference.

The FET labeled oligonucleotide may be structured in a variety of different ways, so long as it includes the above-described donor, acceptor and target nucleic acid binding domains. Typically, the FET labeled oligonucleotide is structured such that energy transfer occurs between the fluorophore and acceptor of the FET labeled oligonucleotide probe upon fluorophore excitation when the FET labeled oligonucleotide is not hybridized to target nucleic acid.

In certain embodiments, the oligonucleotide is a single stranded molecule that does not form intramolecular structures and in which energy transfer occurs because the spacing of the donor and acceptor provides for energy transfer in the single stranded linear format. In these embodiments, energy transfer also occurs between the fluorophore and acceptor of FET labeled oligonucleotide probe upon fluorophore excitation when the FET labeled oligonucleotide probe is hybridized to a target nucleic acid. Specific examples of such FET labeled oligonucleotide probes include the Taqman™ type probes as described in U.S. Pat. No. 6,248,526, the disclosure of which is herein incorporated by reference (as well as Held et al., Genome Res. (1996) 6:986-994; Holland et al., Proc. Nat'l Acad. Sci. USA (1991) 88:7276-7280; and Lee et al., Nuc. Acids Res. (1993) 21:3761-3766 (1993)). In many of these embodiments, the target nucleic acid binding domain is one that hybridizes to, i.e., is complementary to, a sequence of the template nucleic acid, i.e., the target nucleic acid of the target nucleic acid binding domain is a sequence present in the template nucleic acid.

In other embodiments, the probe oligonucleotides are structured such that energy transfer does not occur between the fluorophore and acceptor of said FET labeled oligonucleotide probe upon fluorophore excitation when the FET labeled oligonucleotide probe is hybridized to a target nucleic acid. Examples of these types of probe structures include: Scorpion probes (as described in Whitcombe et al., (Nature Biotechnology (1999) 17:804-807; U.S. Pat. No. 6,326,145, the disclosure of which is herein incorporated by reference), Sunrise probes (as described in Nazarenko et al., Nuc. Acids Res. (1997) 25:2516-2521; U.S. Pat. No. 6,117,635, the disclosure of which is herein incorporated by reference), Molecular Beacons (Tyagi et al., Nature Biotechnology (1996) 14:303-308; U.S. Pat. No. 5,989,823, the disclosure of which is incorporated herein by reference), and conformationally assisted probes (as described in provisional application Ser. No. 60/138,376, the disclosure of which is herein incorporated by reference). In many of these embodiments, the target binding sequence or domain comprises a hybridization domain complementary to a sequence of the primer extension product.

Since the primer extension reaction mixture produced in the initial step of the subject methods of these particular embodiments is a high fidelity primer extension reaction mixture, it further includes an enzyme having 3'→5' exonuclease activity. In many embodiments, the 3'→5' exonuclease is a polymerase that has 3'→5' exonuclease activity. In many embodiments, the high fidelity nature of the reaction mixture is provided by the presence of a combination of two or more polymerases, at least one of which includes a 3'→5' exonuclease. In certain embodiments, e.g., in 5' nuclease applications, care is taken to ensure that a polymerase having 5'→3' nuclease activity is also included. In many embodiments, the polymerase combination employed includes at least one Family A polymerase and, in many embodiments, a Family A polymerase and a Family B polymerase, where the terms "Family A" and "Family B" correspond to the classification scheme reported in Braithwaite & Ito, Nucleic Acids Res. (1993) 21:787-802. Family A polymerases of interest include. *Thermus aquaticus* polymerases, including the naturally occurring polymerase (Taq) and derivatives and homologues thereof, such as Klentaq (as described in Proc. Natl. Acad. Sci USA (1994) 91:2216-2220); *Thermus thermophilus* polymerases, including the naturally occurring polymerase (Tth) and derivatives and homologues thereof, and the like. Family B polymerases of interest include *Thermococcus litoralis* DNA polymerase (Vent) as described in Perler et al., Proc. Natl. Acad. Sci. USA (1992) 89:5577; *Pyrococcus* species GB-D (Deep Vent); *Pyrococcus furiosus* DNA polymerase (Pfu) as described in Lundberg et al., Gene (1991) 108:1-6, *Pyrococcus woesei* (Pwo) and the like. Of the two types of polymerases employed, the Family A polymerase will typically be present the reaction mixture in an amount greater than the Family B polymerase, where the difference in activity will usually be at least 10-fold, and more usually at least about 100-fold. Accordingly, the reaction mixture will typically comprise from about 0.1 U/μl to 1 U/μl Family A polymerase, usually from about 0.2 to 0.5 U/μl Family A polymerase, while the amount of Family B polymerase will typically range from about 0.01 mU/μl to 10 mU/μl, usually from about 0.05 to 1 mU/μl and more usually from about 0.1 to 0.5 mU/μl, where "U" corresponds to incorporation of 10 nmoles dNTP into acid-insoluble material in 30 min at 74° C.

In certain embodiments, a nucleic acid intercalator is present in the reaction mixture. In certain of these embodiments, the nucleic acid intercalator is bonded to the FET probe, such that it is stably associated with the FET probe under the conditions of use. In many of these embodiments, the FET probes employed in the subject invention include a nucleic acid intercalator covalently bonded to the FET labeled oligonucleotide.

The nucleic acid intercalators of interest function to stabilize the nucleic acid helix formed from the FET labeled oligonucleotide. Covalent binding of nucleic acid intercalators of interest also serve to increase hybrid stability by providing additional binding energy. Furthermore, nucleic acid intercalators of interest provide the FET labeled oligonucleotide greater affinity for its complementary sequence. In addition, nucleic acid intercalators provides exonuclease activity resistance when added to the 3' end of said FET labeled oligonucleotide. The nucleic acid intercalator component of the FET probes of this embodiment may be located at any location of the FET probe, e.g., at the 3' end or the 5' end of said FET labeled oligonucleotide, where in many embodiments the intercalator is covalently bonded to the 3' end, e.g., within at least about 10, such as within about 5 nt residues of the 3' end.

In general, nucleic acid intercalators of interest are aromatic compounds having a flat configuration. They may be cyclic, or polycyclic, particularly polycyclic aromatic having at least two rings, usually at least three rings and not more than about six rings, more usually not more than about five rings, where at least two of the rings are fused, usually at least three of the rings are fused, and usually not more than four of the rings being fused. The aromatic compound may be carbocyclic or heterocyclic, particularly having from one to three, more usually one to two nitrogen atoms as heteroannular atoms. Other heterannular atoms may include oxygen and sulfur (chalcogen). The rings may be substituted by a wide variety of substituents, which substituents may include alkyl groups of from one to four carbon atoms, usually from one to two carbon atoms, oxy, which includes hydroxy, alkoxy and carboxy ester, generally of from one to four carbon atoms, amino, including mono- and disubstituted amino, particularly mono- and dialkyl amino, of from 0 to 8, usually 0 to 6 carbon atoms, thio, particularly alkylthio from 1 to 4, usually 1 to 2 carbon atoms, cyano, non-oxo-carbonyl, such as carboxy and derivatives thereof, particularly carboxamide or carboxyalkyl, of from 1 to 8 or 1 to 6 carbon atoms, usually 2 to 6 carbon atoms and more usually 2 to 4 carbon atoms, oxocarbonyl or acyl, generally from 1 to 4 carbon atoms, halo, particularly of atomic number 9 to 35, etc.

Polycyclic compounds which find use as nucleic acid intercalators include acridines, phenanthridines, porphyrins, phenylindoles, and bisbenzamides.

The intercalator may be covalently bonded to the FET labeled oligonucleotide using any convenient protocol, which may or may not employ a linker group, where representative protocols include those protocols provided herein for covalent bonding of the fluorescer/quencher moieties to the FET labeled probes.

DNA intercalators are further described in U.S. Pat. No. 6,280,933; the disclosure of which is herein incorporated by reference.

In certain embodiments, another component of the reaction, mixture produced in the first step of the subject methods is a minor groove binder. Minor groove, binders of interest are those capable of binding isohelically into the minor groove of double stranded DNA by fitting edge-on into the minor groove, replacing the spine of hydration and following the natural curvature of the DNA. This type of molecular recognition is at least partially driven by formation of hydrogen bonds between the minor groove binder and the DNA. The minor groove binders of interest form bifurcated hydrogen bonds with nucleotide base pairs, and numerous van der Waals contacts with various atoms in the nucleotide backbone. These atomic interactions stabilize the DNA-minor groove binder structure and, in turn, effectively strengthen the interaction of the two DNA strands of the helix.

In general, minor groove binders of interest are those capable of binding within the minor groove of a DNA helix with an association constant of $10^3 M^{-1}$ or greater, as determined by using the assay described in Taquet et al., Biochemistry 1998 Jun. 23; 37(25):9119-26. The minor groove binders have a strong preference for A-T (adenine and thymine) rich regions of double stranded DNA. However, minor groove binders which show preference to C-G (cytosine and guanine) rich regions are also of interest. Generally, minor groove binders of interest stabilize A-T hydrogen bonds more than C-G bonds, (thus stabilizing weaker sequences). Minor groove binders form extremely stable duplexes The minor groove binders may be free in the aqueous buffer medium of the primer extension mixture, or bound to the FET labeled oligonucleotide (covalently or non-covalently). The minor groove binder may be linked to a covalent structure or chain of atoms that attaches the minor groove binder to the oligonucleotide. This linking chain can and sometimes is considered as part of the minor groove binder, and does not adversely affect the minor groove binding properties. Furthermore, the minor groove binders may be attached to either the 3' end or the 5' end of the FET labeled oligonucleotide.

In general, minor groove binders have crescent shaped three-dimensional structures, and generally have a molecular weight of between approximately 150 to approximately 2000 Daltons. Examples of minor groove binders include netropsin, distamycin, distamycin A, lexitropsin, mithramycin, chromomycin $A_3$, olivomycin, anthramycin, sibiromycin, pentamidine, stilbamidine, berenil, CC-1065, Hoechst 33258, 4'-6-diamidino-2-phenylindole (DAPI), and derivatives thereof. Typically, the minor groove binder is a N-methylpyrrole peptide such as netropsin and distamycin A. Minor groove binders are further described in U.S. Pat. Nos. 5,801,155 and 5,955,590; the disclosures of which are herein incorporated by reference.

In those embodiments where the minor groove binder is present in the reaction mixture, the amount of minor groove binder present in the reaction mixture typically ranges from about 0.02 µM to about 1.5 µM, usually from about 0.1 µM to about 0.75 µM and more usually from about 0.2 µM to about 0.5 µM.

Another component of the reaction mixture produced in the first step of the subject methods is the template nucleic acid. The nucleic acid that serves as template may be single stranded or double stranded, where the nucleic acid is typically deoxyribonucleic acid (DNA). The length of the template nucleic acid may be as short as 50 bp, but usually be at least about 100 bp long, and more usually at least about 150 bp long, and may be as long as 10,000 bp or longer, e.g., 50,000 bp in length or longer, including a genomic DNA extract, or digest thereof, etc. The nucleic acid may be free in solution, flanked at one or both ends with non-template nucleic acid, present in a vector, e.g. plasmid and the like, with the only criteria being that the nucleic acid be available for participation in the primer extension reaction. The template nucleic acid may be present in purified form, or in a complex mixture with other non-template nucleic acids, e.g., in cellular DNA preparation, etc.

The template nucleic acid may be derived from a variety of different sources, depending on the application for which the PCR is being performed, where such sources include organisms that comprise nucleic acids, i.e. viruses; prokaryotes, e.g. bacteria, archaea and cyanobacteria; and eukaryotes, e.g. members of the kingdom protista, such as flagellates, amoebas and their relatives, amoeboid parasites, ciliates and the like; members of the kingdom fungi, such as slime molds, acellular slime molds, cellular slime molds, water molds, true molds, conjugating, fungi, sac fungi, club fungi, imperfect fungi and the like, plants, such as algae, mosses, liverworts, hornworts, club mosses, horsetails, ferns, gymnosperms and flowering plants, both monocots and dicots; and animals, including sponges, members of the phylum cnidaria, e.g. jelly fish, corals and the like, combjellies, worms, rotifers, roundworms, annelids, molluscs, arthropods, echinoderms, acorn worms, and vertebrates, including reptiles, fishes, birds, snakes, and mammals, e.g. rodents, primates, including humans, and the like. The template nucleic acid may be used directly from its naturally occurring source and/or preprocessed in a number of different ways, as is known in the art. In some embodiments, the template nucleic acid may be from a synthetic source.

The next component of the reaction mixture produced in the first step of the subject methods is the primers employed in the primer extension reaction, e.g., the PCR primers (such as forward and reverse primers employed in geometric amplification or a single primer employed in a linear amplification). The oligonucleotide primers with which the template nucleic acid (hereinafter referred to as template DNA for convenience) is contacted will be of sufficient length to provide for hybridization to complementary template DNA under annealing conditions (described in greater detail below) but will be of insufficient length to form stable hybrids with template DNA under polymerization conditions. The primers will generally be at least 10 bp in length, usually at least 15 bp in length and more usually at least 16 bp in length and may be as long as 30 bp in length or longer, where the length of the primers will generally range from 18 to 50 bp in length, usually from about 20 to 35 bp in length. The template DNA may be contacted with a single primer or a set of two primers (forward and reverse primers), depending on whether primer extension, linear or exponential amplification of the template DNA is desired. Where a single primer is employed, the primer will typically be complementary to one of the 3' ends of the template DNA and when two primers are employed, the primers will typically be complementary to the two 3' ends of the double stranded template DNA.

In addition to the above components, the reaction mixture produced in the subject methods includes deoxyribonucleoside triphosphates (dNTPs). Usually, the reaction mixture will comprise four different types of dNTPs corresponding to the four naturally occurring bases are present, i.e. dATP, dTTP, dCTP and dGTP. In the subject methods, each dNTP will typically be present in an amount ranging from about 10 to 5000 µM, usually from about 20 to 1000 µM.

The reaction mixture prepared in the first step of the subject methods further includes an aqueous buffer medium that includes a source of monovalent ions, a source of divalent cations and a buffering agent. Any convenient source of monovalent ions, such as KCl, K-acetate, $NH_4$-acetate, K-glutamate, $NH_4Cl$, ammonium sulfate, and the like may be employed. The divalent cation may be magnesium, manganese, zinc and the like, where the cation will typically be magnesium. Any convenient source of magnesium cation may be employed, including $MgCl_2$, Mg-acetate, and the like. The amount of $Mg^{2+}$ present in the buffer may range from 0.5 to 10 mM, but will preferably range from about 3 to 6 mM, and will ideally be at about 5 mM. Representative buffering agents or salts that may be present in the buffer include Tris, Tricine, HEPES, MOPS and the like, where the amount of buffering agent will typically range from about 5 to 150 mM, usually from about 10 to 100 mM, and more usually from about 20 to 50 mM, where in certain preferred embodiments the buffering agent will be present in an amount sufficient to provide a pH ranging from about 6.0 to 9.5, where most preferred is pH 7.3 at 72° C. Other agents which may be present in the buffer medium include chelating agents, such as EDTA, EGTA and the like.

In preparing the reaction mixture, the various constituent components may be combined in any convenient order. For example, the buffer may be combined with primer, polymerase and then template DNA, or all of the various constituent components may be combined at the same time to produce the reaction mixture.

Preparation of Non-High Fidelity Reaction Mixture

As indicated above, in certain embodiments, e.g., where a DNA intercalator and/or a minor groove binder is present, the reaction mixture need not be a high fidelity reaction mixture. In these embodiments, the reaction mixture is prepared as described above, but the polymerase having 3'→5' exonuclease activity, e.g., the Family B polymerases reviewed above, is not included in the reaction mixture.

Subjecting the Primer Extension Mixture to Primer Extension Reaction Conditions

Following preparation of the reaction mixture, the reaction mixture is subjected to primer extension reaction conditions, i.e., to conditions that permit for polymerase mediated primer extension by addition of nucleotides to the end of the primer molecule using the template strand as a template. In many embodiments, the primer extension reaction conditions are amplification conditions, which conditions include a plurality of reaction cycles, where each reaction cycle comprises: (1) a denaturation step, (2) an annealing step, and (3) a polymerization step. The number of reaction cycles will vary depending on the application being performed, but will usually be at least 15, more usually at least 20 and may be as high as 60 or higher, where the number of different cycles will typically range from about 20 to 40. For methods where more than about 25, usually more than about 30 cycles are performed, it may be convenient or desirable to introduce additional polymerase into the reaction mixture such that conditions suitable for enzymatic primer extension are maintained.

The denaturation step comprises heating the reaction mixture to an elevated temperature and maintaining the mixture at the elevated temperature for a period of time sufficient for any double stranded or hybridized nucleic acid present in the reaction mixture to dissociate. For denaturation, the temperature of the reaction mixture will usually be raised to, and maintained at, a temperature ranging from about 85 to 100, usually from about 90 to 98 and more usually from about 93 to 96° C. for a period of time ranging from about 3 to 120 sec, usually from about 5 to 30 sec.

Following denaturation, the reaction mixture will be subjected to conditions sufficient for primer annealing to template DNA present in the mixture. The temperature to which the reaction mixture is lowered to achieve these conditions will usually be chosen to provide optimal efficiency and specificity, and will generally range from about 50 to 75, usually from about 55 to 70 and more usually from about 60 to 68° C. Annealing conditions will be maintained for a period of time ranging from about 15 sec to 30 min, usually from about 30 sec to 5 min.

Following annealing of primer to template DNA or during annealing of primer to template DNA, the reaction mixture will be subjected to conditions sufficient to provide for polymerization of nucleotides to the primer ends in manner such that the primer is extended in a 5' to 3' direction using the DNA to which it is hybridized as a template, i.e., conditions sufficient for enzymatic production of primer extension product. To achieve polymerization conditions, the temperature of the reaction mixture will typically be raised to or maintained at a temperature ranging from about 65 to 75, usually from about 67 to 73° C. and maintained for a period of time ranging from about 15 sec to 20 min, usually from about 30 sec to 5 min.

The above cycles of denaturation, annealing and polymerization may be performed using an automated device, typically known as a thermal cycler. Thermal cyclers that may be employed are described in U.S. Pat. Nos. 5,612,473; 5,602, 756; 5,538,871; and 5,475,610, the disclosures of which are herein incorporated by reference.

Signal Detection

The next step in the subject methods is signal detection, i.e., detecting a change in a fluorescent signal from the FET labeled oligonucleotide probe present in the reaction mixture to obtain an assay result. In other words, the next step in the subject methods is to detect any modulation in the fluorescent signal generated by the FET labeled oligonucleotide present in the reaction mixture. The change may be an increase or decrease in fluorescence, depending on the nature of the label employed, but in many embodiments is an increase in fluorescence. The sample may be screened for an increase in fluorescence using any convenient means, e.g., a suitable fluorimeter, such as a thermostable-cuvette or plate-reader fluorimeter. Fluorescence is suitably, monitored using a known fluorimeter. The signals from these devices, for instance in the form of photo-multiplier voltages, are sent to a data processor board and converted into a spectrum associated with each sample tube. Multiple tubes, for example 96 tubes, can be assessed at the same time. Data may be collected in this way at frequent intervals, for example once every 10 ms, throughout the reaction. By monitoring the fluorescence of the reactive molecule from the sample during each cycle, the progress of the amplification reaction can be monitored in various ways. For example, the data provided by melting peaks can be analyzed, for example by calculating the area under the melting peaks and this data plotted against the number of cycles.

The spectra generated in this way can be resolved, for example, using "fits" of pre-selected fluorescent moieties such as dyes, to form peaks representative of each signaling moiety (i.e. fluorophore). The areas under the peaks can be determined which represents the intensity value for each signal, and if required, expressed as quotients of each other. The differential of signal intensities and/or ratios will allow changes in FET to be recorded through the reaction or at different reaction conditions, such as temperatures. The changes are related to the binding phenomenon between the oligonucleotide probe and the target sequence or degradation of the oligonucleotide probe bound to the target sequence. The integral of the area under the differential peaks will allow intensity values for the FET effects to be calculated.

Screening the mixture for a change in fluorescence provides one or more assay results, depending on whether the sample is screened once at the end of the primer extension reaction, or multiple times, e.g., after each cycle, of an amplification reaction (e.g., as is done in real time PCR monitoring).

Employing Said Assay Result to Determine Whether a Primer Extension Product is Present in Said Mixture The data generated as described above can be interpreted in various ways. In its simplest form, an increase or decrease in fluorescence from the sample in the course of or at the end of the amplification reaction is indicative of an increase in the amount of the target sequence present, i.e., primer extension product present, suggestive of the fact that the amplification reaction has proceeded and therefore the target sequence was in fact present in the sample. Quantitation is also possible by monitoring the amplification reaction throughout the amplification process.

In this manner, a reaction mixture is readily screened for the presence of primer extension products. The methods are suitable for detection of a single primer extension product as well as multiplex analyses, in which two or more different FET labeled oligonucleotide probes are employed to screen for two or more different primer extension products. In these latter multiplex situations, the number of different types of probes that may be employed typically ranges from about 2 to about 20 or higher, usually from about 2 to about 15.

The above described methods of detecting the presence of one or more types of primer extension reaction products in a primer extension reaction mixture finds use in a variety of different applications, representative ones of which are now reviewed in greater detail.

Utility

The above-described inventive methods find use in a variety of different applications. In general, the subject oligonucleotide probes and methods of using the same find use in any high fidelity primer extension reaction in which a FET probe and proofreading polymerase are employed.

One type of representative application is in monitoring the progress of nucleic acid amplification reactions, such as polymerase chain reaction applications, including both linear and geometric PCR applications. As used herein, the term monitoring includes a single evaluation at the end of a series of reaction cycles as well as multiple evaluations, e.g., after each reaction cycle, such that the methods can be employed to determine whether a particular amplification reaction series has resulted in the production of primer extension product, e.g., a non-real time evaluation, as well as in a real-time evaluation of the progress of the amplification reaction.

The subject methods find use in both 5' nuclease methods of monitoring a PCR amplification reaction (e.g., where a Taqman type probe is employed); and non-5' nuclease methods of monitoring a PCR amplification reaction (e.g., where a molecular beacon type probe is employed). Again, the subject methods find use in evaluating the progress of an amplification reaction at a single time (e.g., non-real time monitoring) and in real-time monitoring.

Monitoring a PCR reaction according to the subject methods finds use in a variety of specific applications. Representative applications of interest include, but are not limited to: (1) detection of allelic polymorphism; (2) SNP detection; (3) detection of rare mutations; (4) detection of allelic stage of single cells; (5) detection of single or low copy number DNA analyte molecules in a sample; etc. For example, in detection of allelic polymorphism, a nucleic acid sample to be screened, e.g., a genomic DNA cellular extract, is employed as template nucleic acid in the preparation of a primer extension reaction mixture, as described above, where the reaction mixture includes a different and distinguishable FET labeled oligonucleotide probe that is specific for each different allelic sequence to be identified, if present. The assay is then carried out as described above, where the sample is screened for a change in signal from each different oligonucleotide probe. A change in signal from a given probe is indicative of the presence the allelic variant to which that probe is specific in the sample. Likewise, an absence of change in signal is indicative of the absence of the allelic variant in the sample. In this manner, the sample is readily screened for the presence of one or more allelic variants. A similar approach can be used for SNP detection, where a different FET labeled oligonucleotide for each SNP of interest to be screened in a nucleic acid sample is employed.

A significant benefit of employing the subject methods in PCR screening applications is that the PCR conditions may be "high fidelity," i.e., they may include a proof reading activity, such that the results obtained from the assays performed according to the subject methods are highly reliable.

Kits

Also provided are kits for practicing the subject methods. The kits according to the present invention will comprise at least: (a) a FET labeled oligonucleotide, where the kits may include two or more distinguishable FET labeled oligonucleotides, e.g., that hybridize to different target nucleic acids, e.g., two or more different SNPs; and (b) instructions for using the provide FET labeled oligonucleotide(s) in a high fidelity amplification, e.g., PCR, reaction.

The subject kits may further comprise additional reagents which are required for or convenient and/or desirable to include in the reaction mixture prepared during the subject methods, where such reagents include: one or more polymerases, including a polymerase mix, where the one or more polymerases at least include a polymerase that exhibits proofreading, i.e., 3'→5' exonuclease activity in certain embodiments; an aqueous buffer medium (either prepared or present in its constituent components, where one or more of the components may be premixed or all of the components may be separate), and the like.

The various reagent components of the kits may be present in separate containers, or may all be precombined into a reagent mixture for combination with template DNA. For example, the kit may include an intercalator-FET probe and a minor groove binder, where these two components may be present separately or combined into a single composition for use.

In addition to the above components, the subject kits will further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, etc., on which the information has been recorded. Yet another means that may be present is a website address which may be used via the internet to access the information at a removed site. Any convenient means may be present in the kits.

Systems

Also provided are systems for use in practicing the subject methods. The subject systems at least include one or more FET labeled oligonucleotides and a proofreading activity, as well as any other requisite components for preparing a primer extension reaction mixture, as described above. In addition, the subject systems may include any required devices for practicing the subject methods, e.g., thermal cyclers, fluorimeters, etc.

The following examples are offered by way of illustration and not by way of limitation.

EXPERIMENTAL PROCEDURES

A. General

The oligonucleotides shown in Table 1 were used for the following example. Standard DNA phosphoramidites, including 6-carboxy-fluorescein (6-FAM) phosphoramidite, 5'-Tetrachloro-Fluorescein (TET) phosphoramidite, and 6-carboxytetramethyl-rhodamine (TAMRA) CPG, 3'-Dabcyl CPG, were obtained from Glen Research. Black Hole Quenchers (BHQ1, BHQ2, BHQ3) CPG were obtained from Biosearch Technology. Eclipse Dark Quencher (eDQ) CPG was obtained from Epoch Bioscience. All primers were purified using Oligo Purification Cartridges (Biosearch Technology). Doubly labeled FET probes were synthesized using CPGs with various quenchers as indicated in Table 1 and with either 6'FAM-labeled or TET-labeled phosphoramidites at the 5' end. The doubly labeled FET probes were purified by preparative HPLC and PAGE using standard protocols. Phosphorothioate modification was prepared by standard procedure.

TABLE I

Sequence Listing

| Name | | Type | Sequence |
|---|---|---|---|
| BCL-F1 | SEQ ID NO: 1 | Primer | 5' GGT GGT GGA GGA GCT CTT CAG 3' |
| BCL-R1 | SEQ ID NO: 2 | Primer | 5' CCA GCC TCC GTT ATC CTG GA 3' |
| BCL-P1 | SEQ ID NO: 3 | Probe | 5' FAM-CCT GTG GAT GAC TGA GTA CCT GAA CCG-BHQ1-3' |
| BCL-P2 | SEQ ID NO: 4 | Probe | 5' FAM-CCT GTG GAT GAC TGA GTA CCT GAA CCG-eDQ-3' |
| BCL-P3 | SEQ ID NO: 5 | Probe | 5' FAM-CCT GTG GAT GAC TGA GTA CCT GAA CCG-DABCYL-3' |
| BCL-P4 | SEQ ID NO: 6 | Probe | 5' FAM-CCT GTG GAT GAC TGA GTA CCT GAA CCG-TAMRA-3' |
| BCL-P5 | SEQ ID NO: 7 | S-oligo Probe | 5' FAM-CCT GTG GAT GAC TGA GTA CCT GAA*C*C*G-TAMRA-3' |
| ACT-F1 | SEQ ID NO: 8 | Primer | 5' GAG CTA CGA GCT GCC TGA C 3' |
| ACT-R1 | SEQ ID NO: 9 | Primer | 5' GAC TCC ATG CCC AGG AAG 3' |
| ACT-P1 | SEQ ID NO: 10 | Probe | 5' TET-CAT CAC CAT TGG CAA TGA GCG-BHQ1-3' |
| ACT-P2 | SEQ ID NO: 11 | Probe | 5' TET-CAT CAC CAT TGG CAA TGA GCG-eDQ-3' |
| ACT-P3 | SEQ ID NO: 12 | Probe | 5' TET-CAT CAC CAT TGG CAA TGA GCG-DABCYL-3' |
| ACT-P4 | SEQ ID NO: 13 | Probe | 5' TET-CAT CAC CAT TGG CAA TGA GCG-TAMRA-3' |
| ACT-P5 | SEQ ID NO: 14 | S-oligo Probe | 5' TET-CAT CAC CAT TGG CAA TGA *G*C*G-TAMRA-3' |

TABLE I-continued

Sequence Listing

| Name | | Type | Sequence |
|---|---|---|---|
| ABCG-R1 | SEQ ID NO: 15 | Primer | 5' CCC AAA AAT TCA TTA TGC TGC AA 3' |
| ABCG-P1 | SEQ ID NO: 16 | Primer | 5' FAM-CAG CAT TCC ACG ATA TGG ATT TAC GGC-BHQ1-3' |
| ABCG-P2 | SEQ ID NO: 17 | Primer | 5' FAM-CAG CAT TCC ACG ATA TGG ATT TAC GGC-TAMRA-3' |
| ABCG-T1 | SEQ ID NO: 18 | Template | 5' ATC AGC ATT CCA CGA TAT GGA TTT ACG GCA TCA GTT GCA GCA TAA TGA ATT TTT GGG A 3' |
| MTHFR-F1 | SEQ ID NO: 19 | Primer | 5' GGA AGA ATG TGT CAG CCT CAA AG 3' |
| MTHFR-R1 | SEQ ID NO: 20 | Primer | 5' CTG ACC TGA AGC ACT TGA AGG AG 3' |
| MTHFR-P1 | SEQ ID NO: 21 | Wt Probe | 5' TET- TGA AAT CGG CTC CCG CA -BHQ1-3' |
| MTHFR-P2 | SEQ 1D NO: 22 | Mut Probe | 5' FAM- TGA AAT CGA CTC CCG CAG A -BHQ1-3' |

*phosphorothioate internucleotide linkage

Example 1

Properties and Use of TET Labeled FET Probes with Various Quenchers

Real Time amplifications and detection were performed in ABI PRISM 7700 (Applied Biosystems) using 30 µl reactions that contained 20 mM Tris-HCl (pH8.3), 60 mM KCl, 5.3 mM MgCl$_2$, 0.2 mM dATP, 0.2 mM dTTP, 0.2 mM dGTP, 0.2 mM dCTP, 0.5 µM of each primer, 0.2 µM FET probe, 4-fold series dilute of Jurkat cDNAs, either 0.6 units Taq Polymerase (Fisher) or a mix of Taq and Pwo DNA Polymerase (Roche Molecular Biochemicals) at unit ratio of 5 to 1.

A 99 basepair segment of the human beta actin gene was amplified using primers ACT-F1 and ACT-R1 listed in Table 1. Thermal profile was 95° C. 15 sec; 50 cycles of 95° C. 15 sec, 60° C. 30 sec, 72° C. 45 sec. After amplification, fluorescent intensity at each well was measured by post PCR reading.

Five types of TET labeled FET probes (ACT-P1, ACT-P2, ACT-P3, ACT-P4 and ACT-P5 as shown in Table 1) were tested in Real Time amplification. Post PCR reading result is shown in Table 2. The emission intensity of donor under condition with template is divided by the emission intensity of donor under condition without template to give +/− signal ratio, which indicates whether the probes are degraded or not. For TET labeled FET probes having TAMRA or Dabcyl as quencher, 3'→5' exonuclease addition caused a dramatic decrease in +/− signal ratio due to cleavage of FET probes.

Figures 1, 1A, 2, 3:
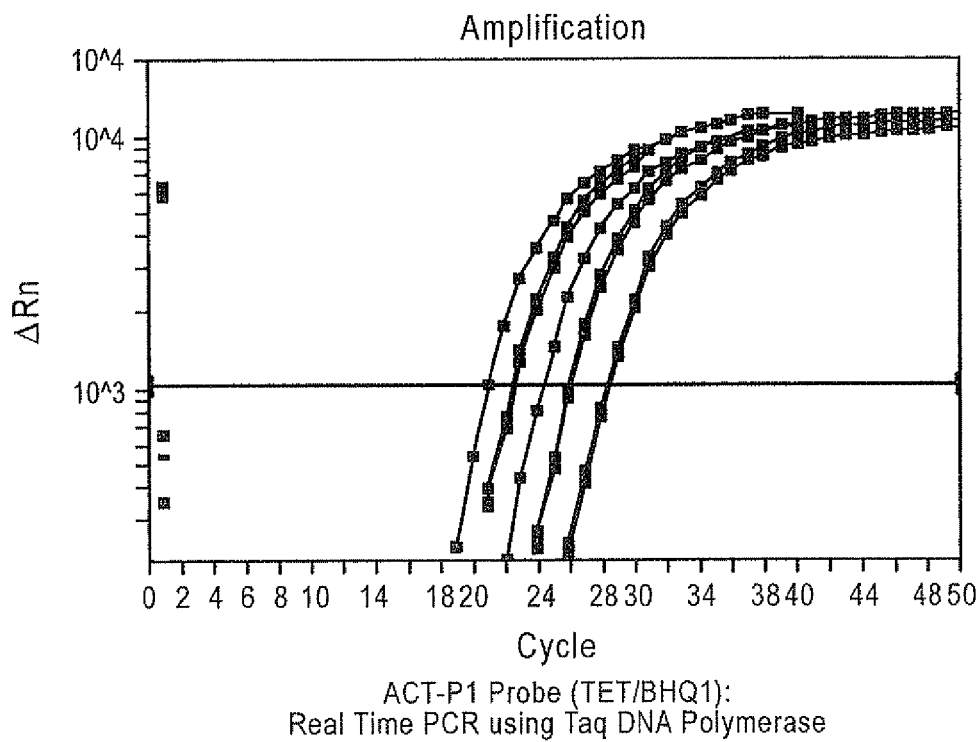
FIG. 3 provides graphical results of a multicomponent analysis of a FAM/TAMRA FET oligo primer and a FAM/BHQ1 FET oligo primer.
Figures 1, 1A, 2, 3, 4:
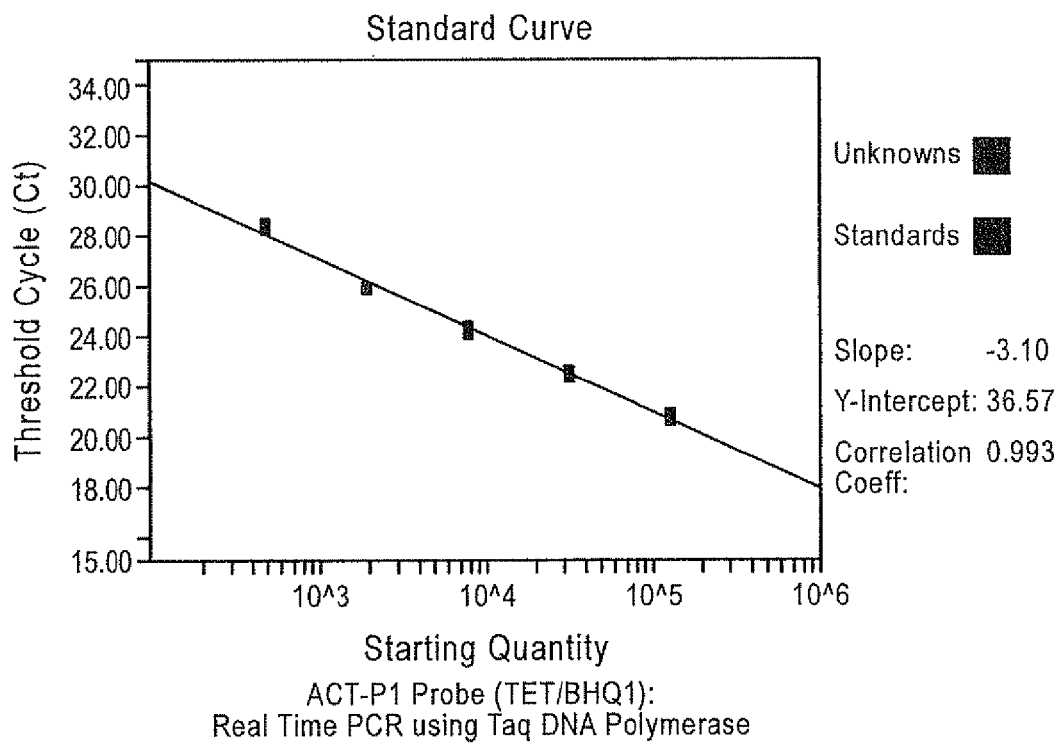
FIG. 4 provides graphical results of assays for allele discrimination using FAM and TET labeled FET probes under high fidelity PCR conditions.
Figures 1, 1B:
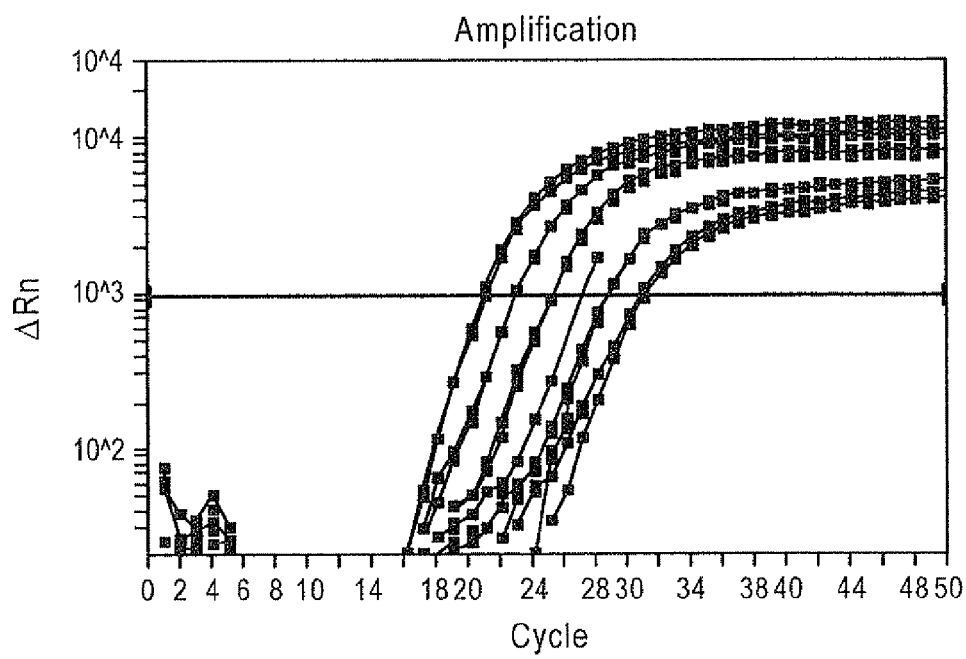
Figures 1, 1B, 2:
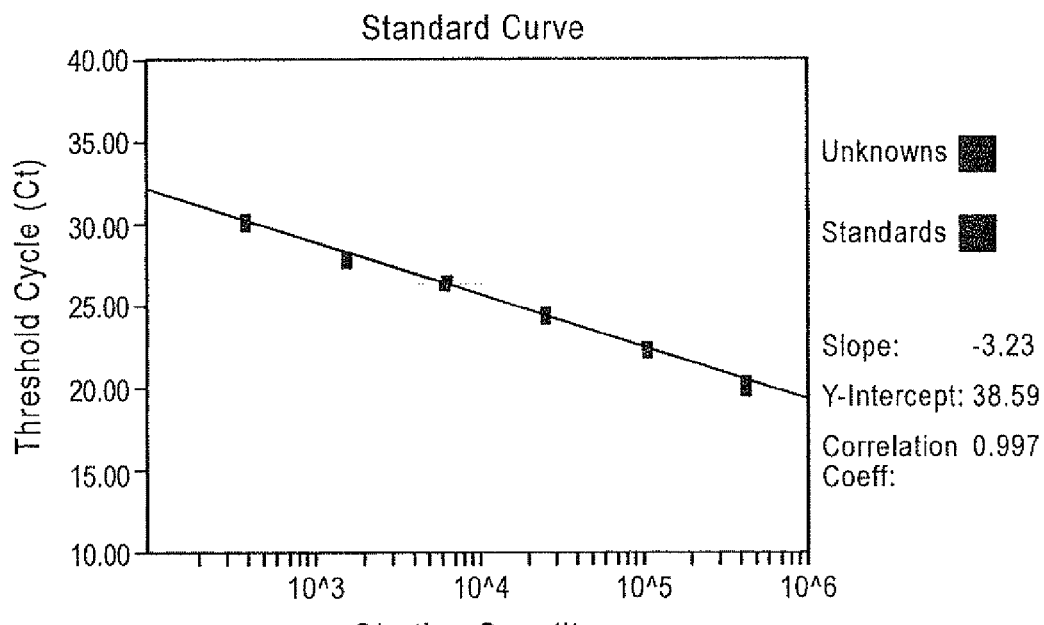
Figures 1, 1B, 2, 3:
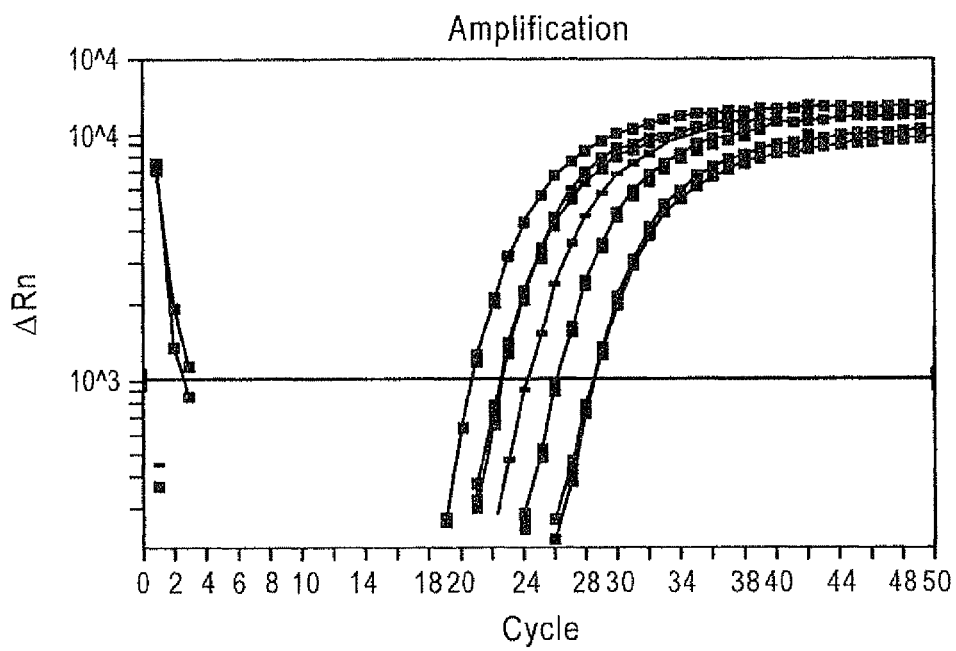
Figures 1, 1B, 2, 3, 4:
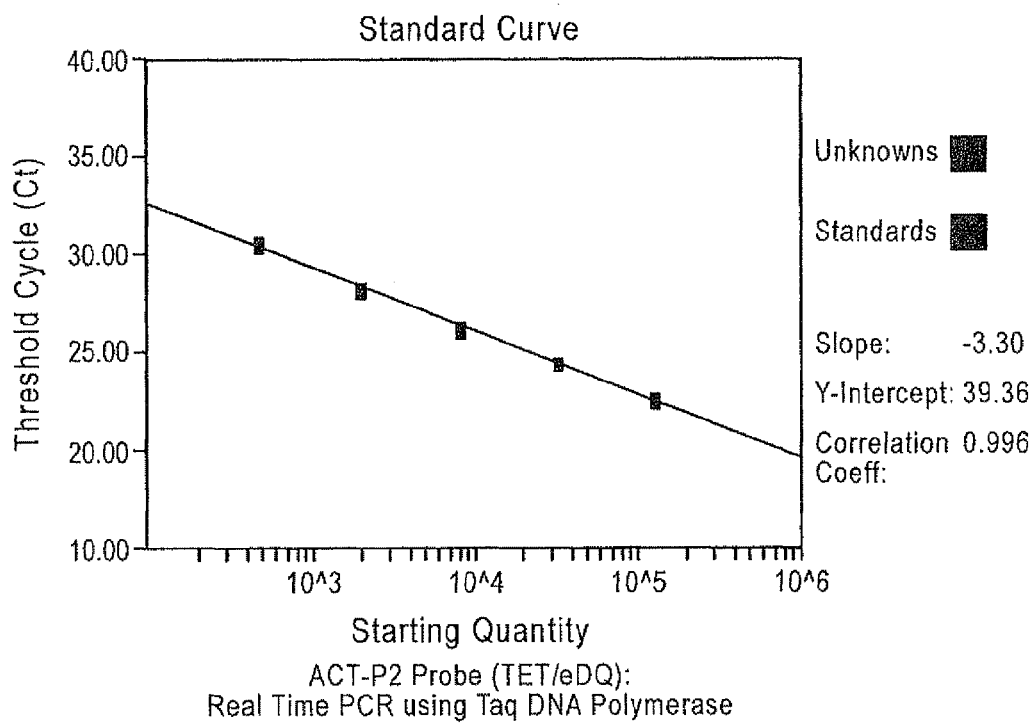
Figures 1, 1C:
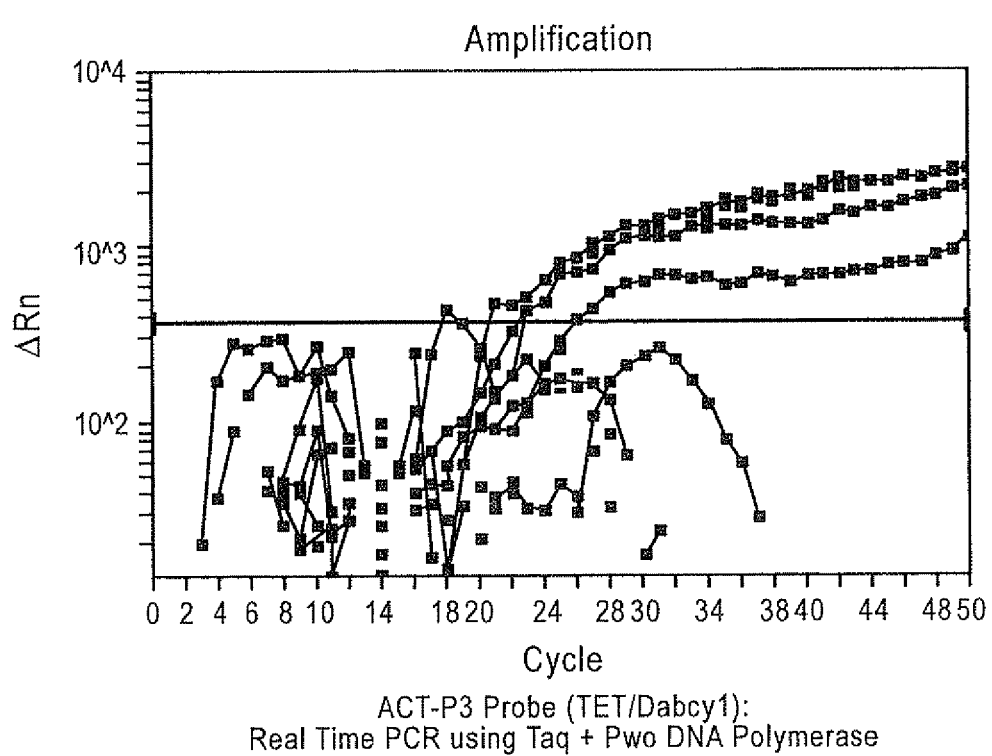
Figures 1, 1C, 2:
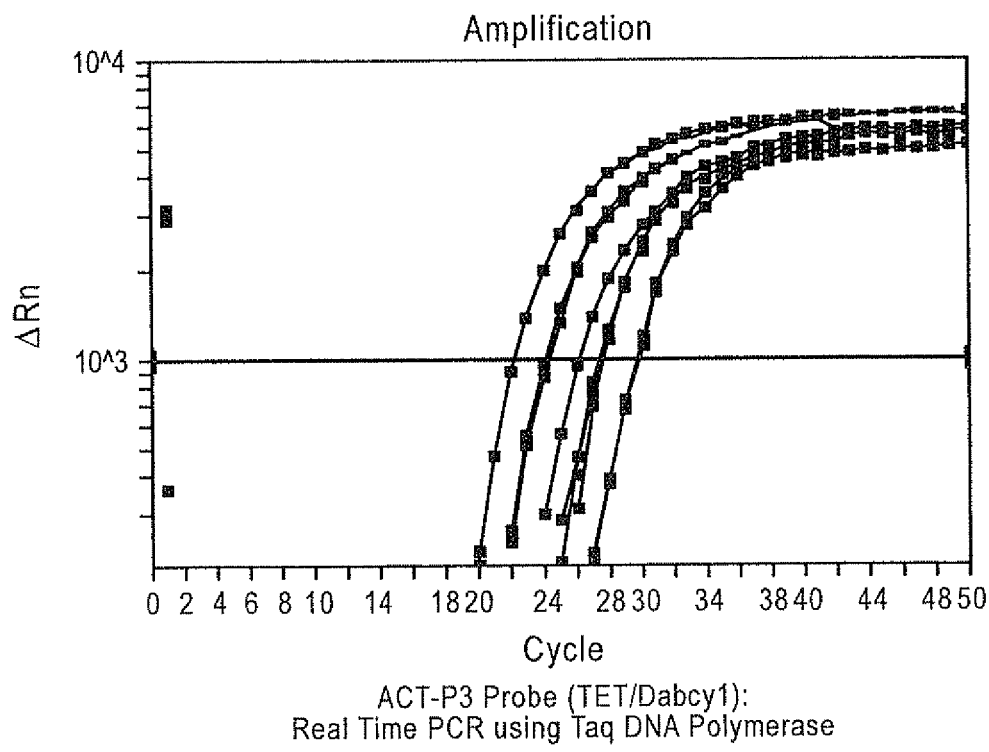
Figures 1, 1C, 2, 3:
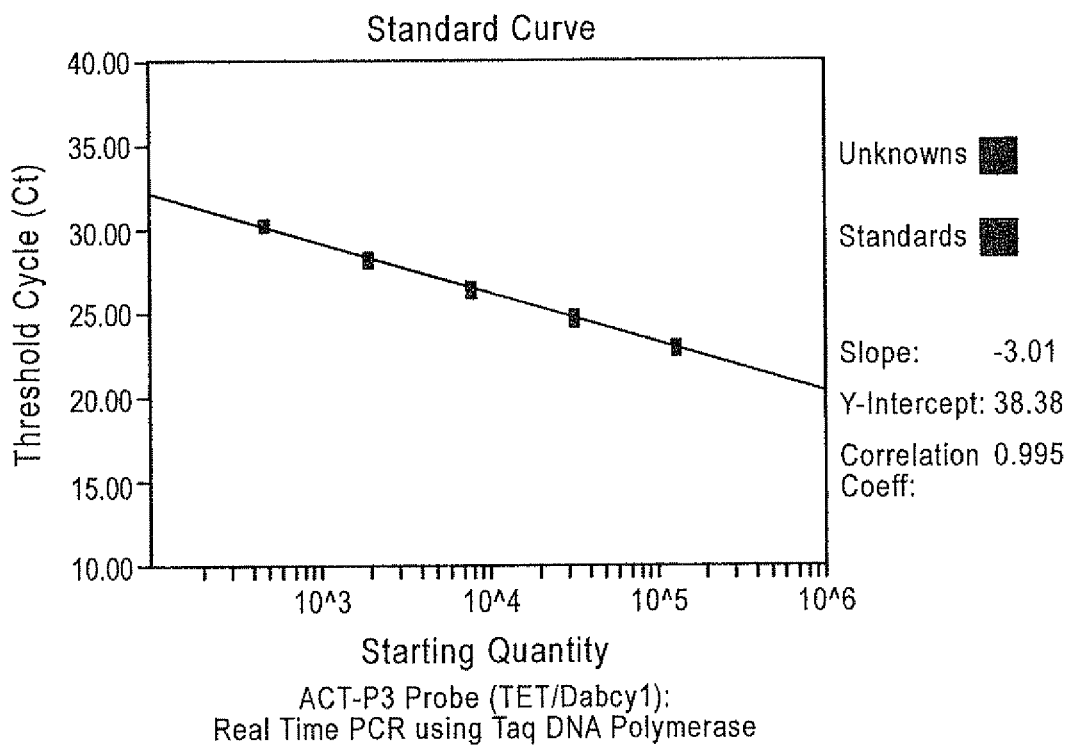
Figures 1, 1D:
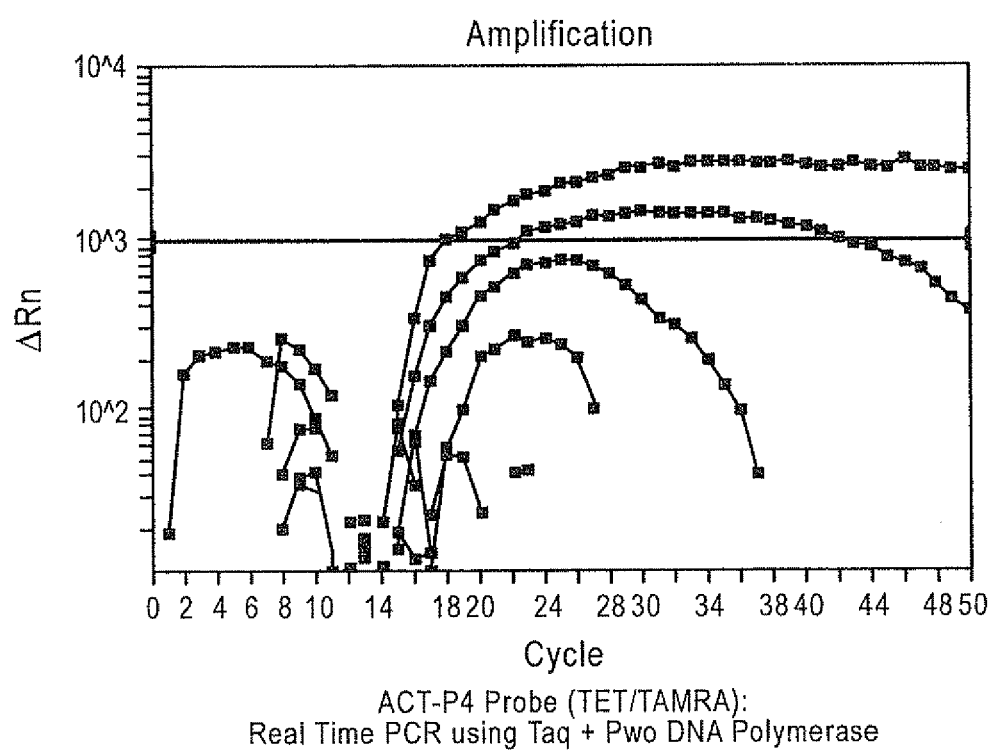
Figures 1, 1D, 2:
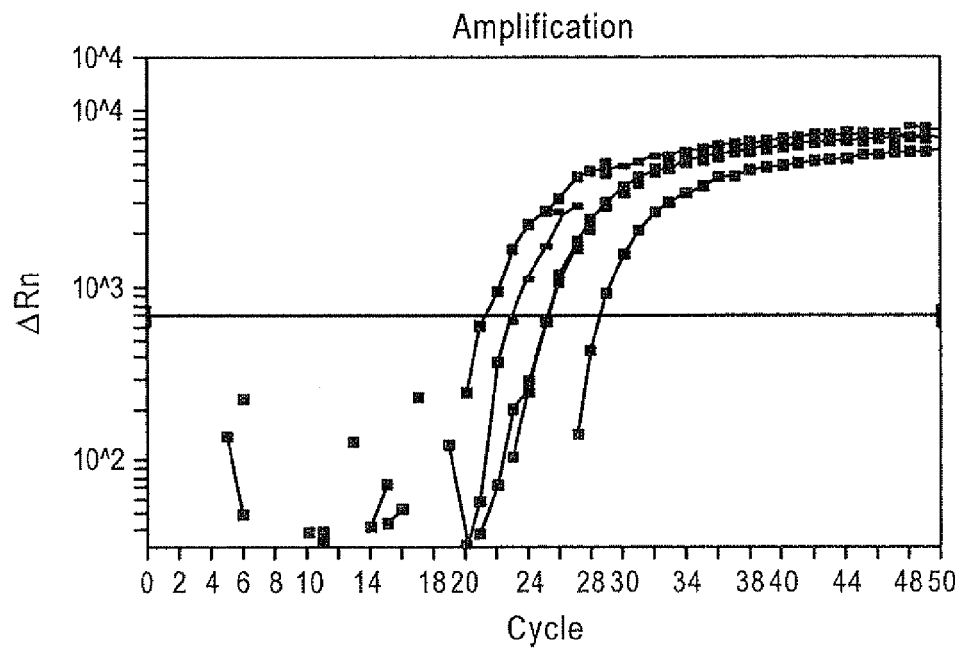
Figures 1, 1D, 2, 3:
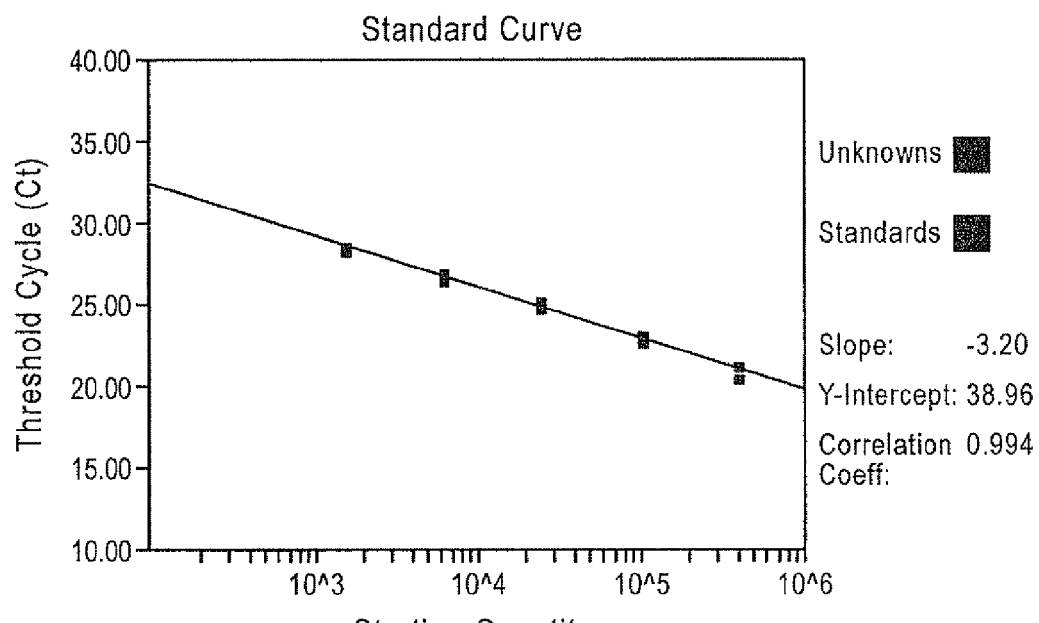
Figures 1, 1E:
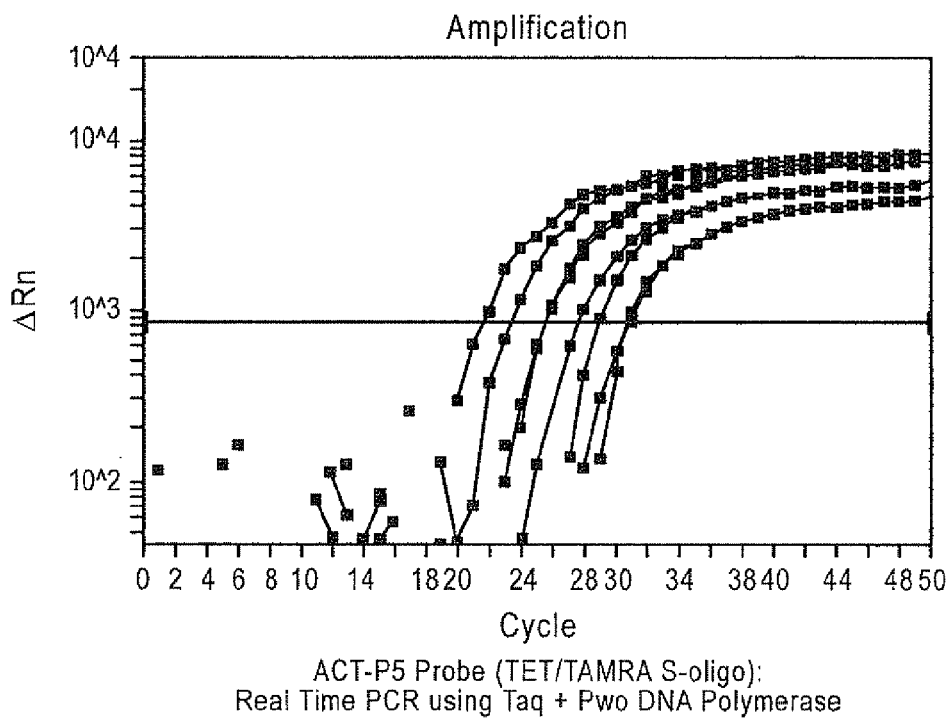
Figures 1, 1E, 2:
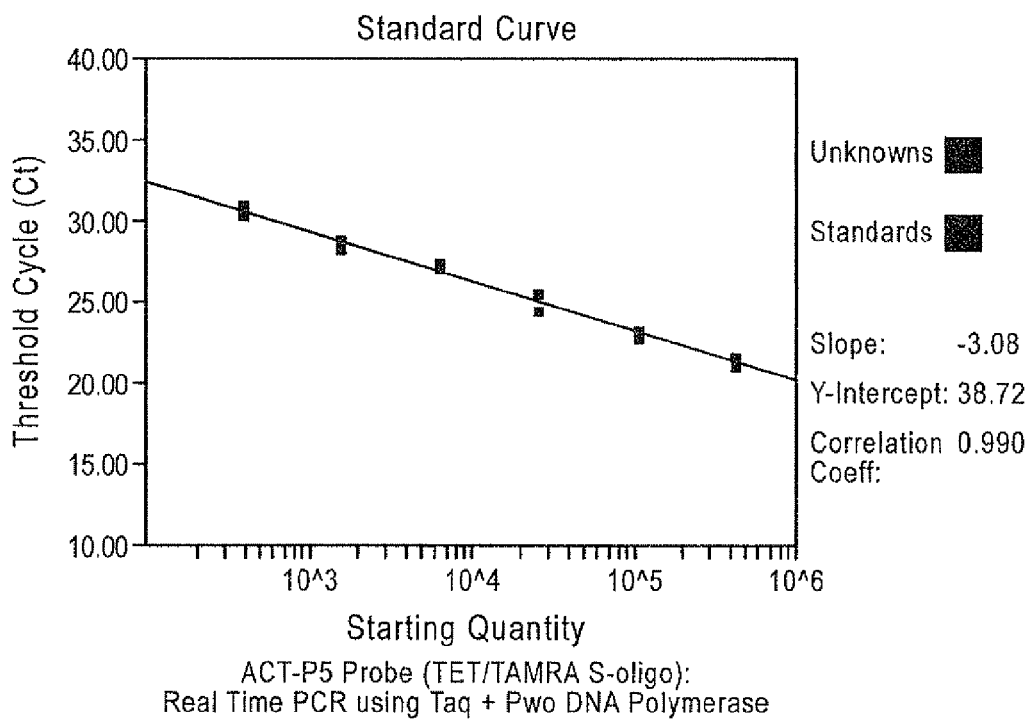
Figures 1, 1E, 2, 3:
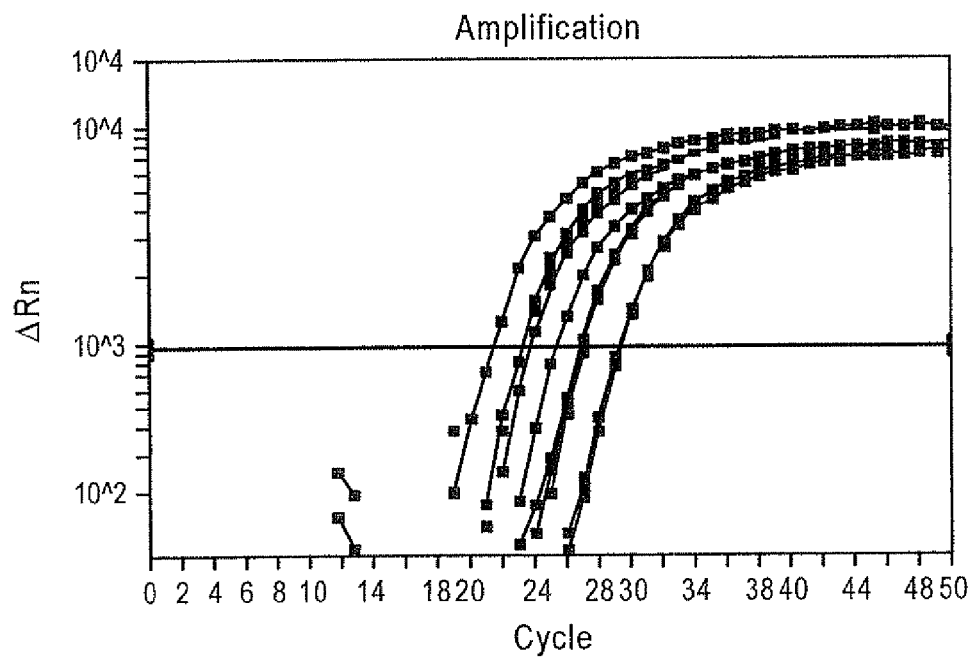
Figures 1, 1E, 2, 3, 4:
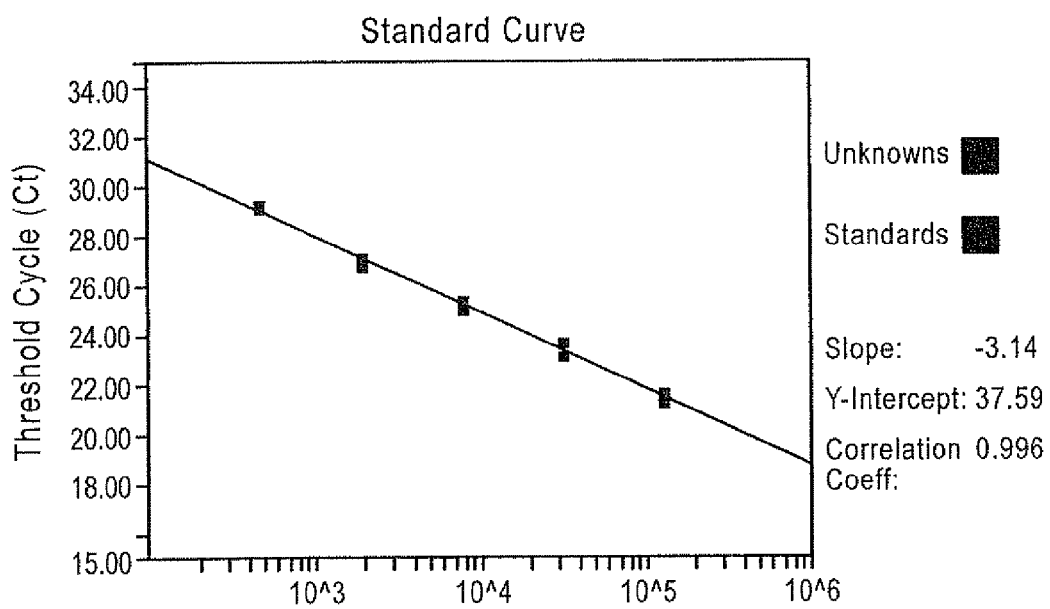

Real Time amplification plot is shown in FIG. 1A-E. TET labeled FET probes having either BHQ1 or Eclipse Dark Quencher at 3'-end are resistant to 3'→5' exonuclease, and are therefore suitable for use in high fidelity PCR (FIGS. 1A and 1B). By contrast, TET labeled FET probes having either TAMRA or Dabcyl Quencher at 3'-end are degraded by 3'→5' exonuclease, and no proper real time PCR results can be obtained (FIGS. 1C and 1D). The TET labeled FET probes having TAMRA Quencher at 3'-end can also be resistant to 3'→5' exonuclease if three phosphorothioate internucleotide linkages at 3'-end are added (FIG. 1E), which confirms the reliability of this whole experiment.

Example 2

Properties and Use of FAM Labeled FET Probes with Various Quenchers

Real Time amplifications and detection were performed in ABI PRISM 7700 using 30 µl reactions that contained 20 mM Tris-HCl (pH8.3), 60 mM KCl, 5.3 mM MgCl$_2$, 0.2 mM dATP, 0.2 mM dTTP, 0.2 mM dGTP, 0.2 mM dCTP, 0.5 uM of each primers, 0.2 µM FET probe, various copies of a cDNA clone of human bcl-2 gene or Jurkat cDNAs, 0.6 units Taq DNA Polymerase (Fisher Scientific) or a mix of Taq and Pwo DNA Polymerase (Roche Molecular Biochemicals) at unit ratio of 10 to 1.

A 190 basepair segment of the human bcl-2 gene was amplified using primers BCL-F1 and BCL-R1 listed in Table

TABLE 2

Fluorescent changes in various TET labeled FET probe during PCR

| | PCR using Taq pol. | | | PCR using Taq + Pwo pol. | | |
|---|---|---|---|---|---|---|
| donor/quencher | no template | Template | +/−signal ratio | no template | template | +/−signal ratio |
| TET/BHQ1 | 4500.0 | 20250.0 | 4.5 | 4500.0 | 20000.0 | 4.4 |
| TET/eDQ | 4000.0 | 20000.0 | 5.0 | 4000.0 | 20000.0 | 5.0 |
| TET/Dabcyl | 6000.0 | 19000.0 | 3.2 | 16000.0 | 24000.0 | 1.5 |
| TET/TAMRA | 3900.0 | 19000.0 | 4.9 | 12000.0 | 18000.0 | 1.5 |
| TET/TAMRA S-oligo | 4000.0 | 20000.0 | 5.0 | 3900.0 | 19000.0 | 4.9 |

1. Thermal profile was 95° C. 15 sec; 50 cycles of 95° C. 15 sec, 60° C. 30 sec, 72° C. 45 sec. After amplification, fluorescent intensity at each well was measured by post PCR reading.

Five types of FAM-labeled FET probes (BCL-P1, BCL-P2, BCL-P3, BCL-P4 and BCL-P5 as shown in Table 1) were tested in Real Time amplification. Post PCR reading result is shown in Table 3. For FAM labeled FET probes having TAMRA or Dabcyl as quencher, 3'→5' exonuclease addition caused a dramatic decrease in +/− signal ratio due to cleavage of FET probes.

Two types of FET primers (ABCG-P1 and ABCG-P2) and a template (ABCG-T1) as listed in Table 1 were tested in Real Time Amplification of human ABC transporter ABCG2. Multicomponent analysis is shown in FIG. 3. Thus, the subject FET labeled nucleic acid detectors having a BHQ1 at 3'-end are resistant to 3'→5' exonuclease activity when used as a primer. By contrast, the FET labeled nucleic acid detectors having a TAMRA at 3'-end are degraded by 3'→5' exonuclease activity. Similar results were obtained using FET primers having mismatch at 3'-end.

TABLE 3

Fluorescent changes in various FAM labeled FET probe during PCR

| donor/quencher | PCR using Taq pol. | | | PCR using Taq + Pwo pol. | | |
|---|---|---|---|---|---|---|
| | no template | template | +/−signal ratio | no template | template | +/−signal ratio |
| FAM/BHQ1 | 5000.0 | 20000.0 | 4.0 | 5000.0 | 20000.0 | 4.0 |
| FAM/eDQ | 5000.0 | 20000.0 | 4.0 | 5000.0 | 19000.0 | 3.8 |
| FAM/Dabcyl | 7000.0 | 20000.0 | 2.9 | 18000.0 | 25000.0 | 1.4 |
| FAM/TAMRA | 5000.0 | 22500.0 | 4.5 | 20000.0 | 30000.0 | 1.5 |
| FAM/TAMRA S-oligo | 10000.0 | 30000.0 | 3.0 | 10000.0 | 29000.0 | 2.9 |

Figures 1, 2A:
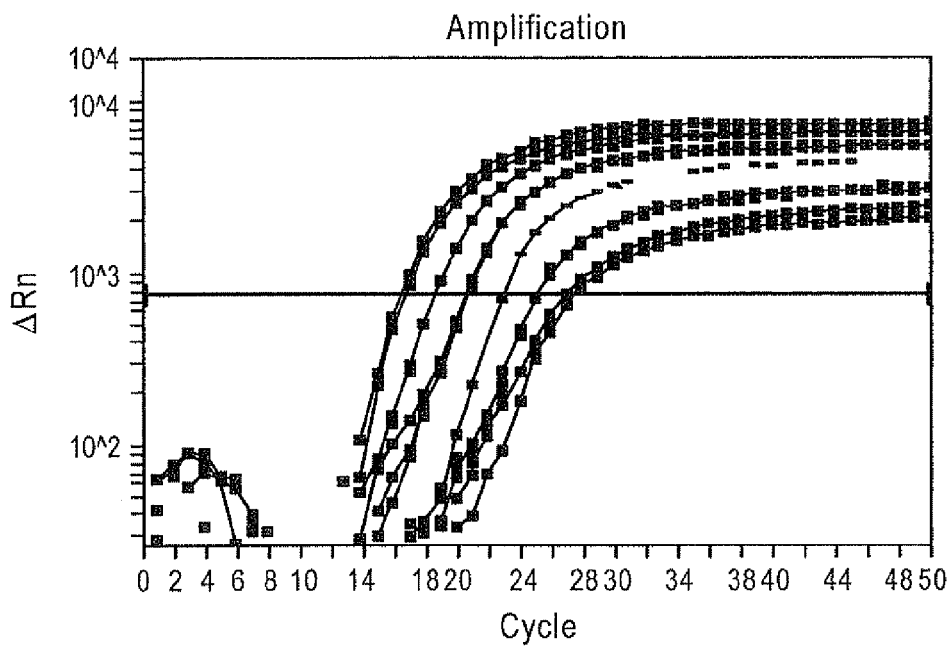
FIGS. 2A to 2B provide graphical results of assays comparing the function of FAM/BHQ1 FET probe and FAM/TAMRA FET probe under high fidelity and standard PCR conditions.
Figures 2, 2A:
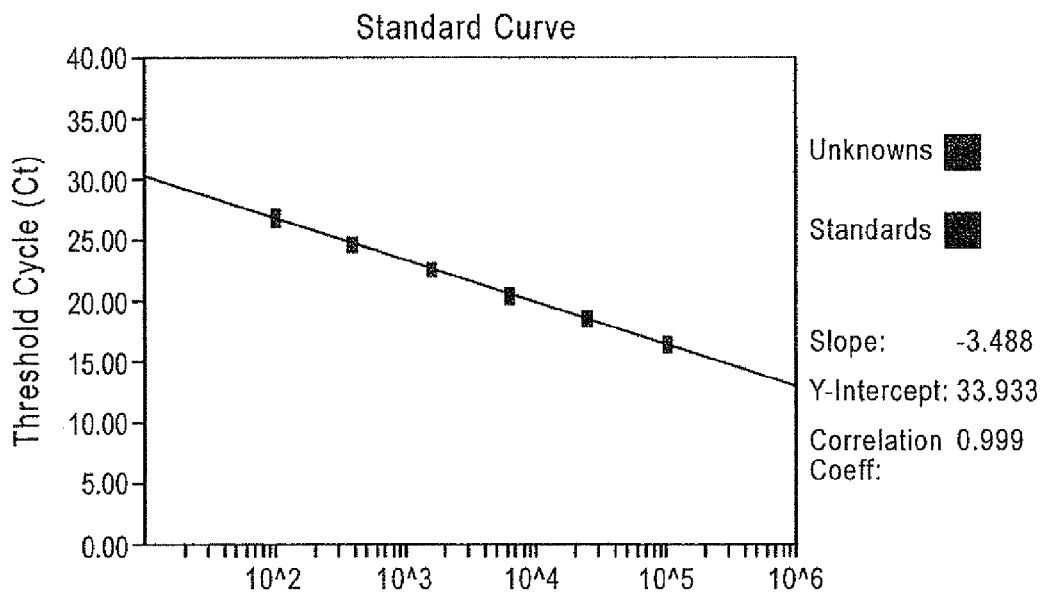
Figures 2, 2A, 3:
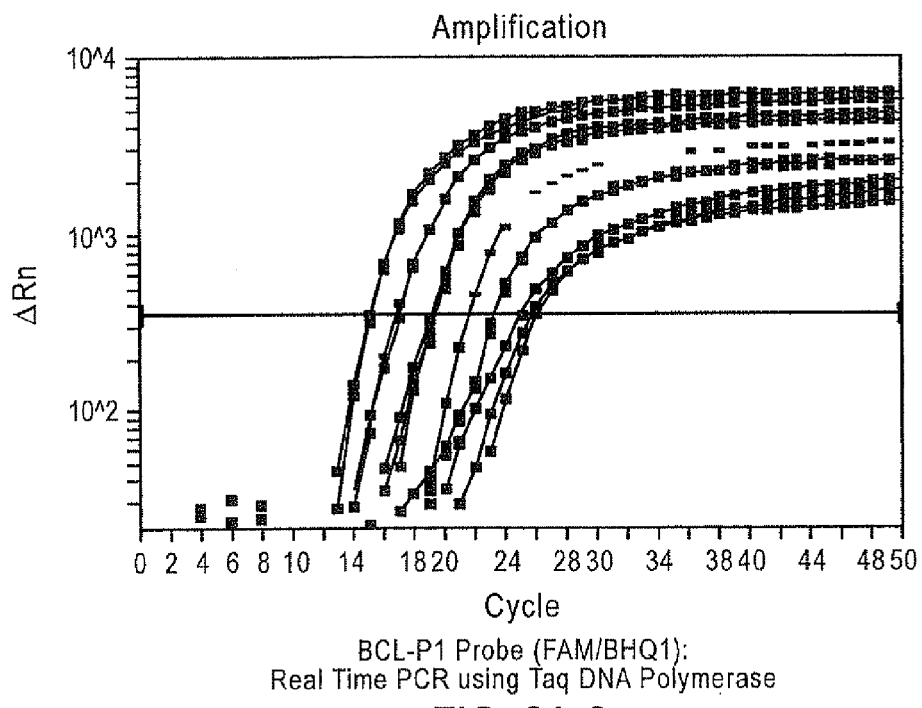
Figures 2, 2A, 3, 4:
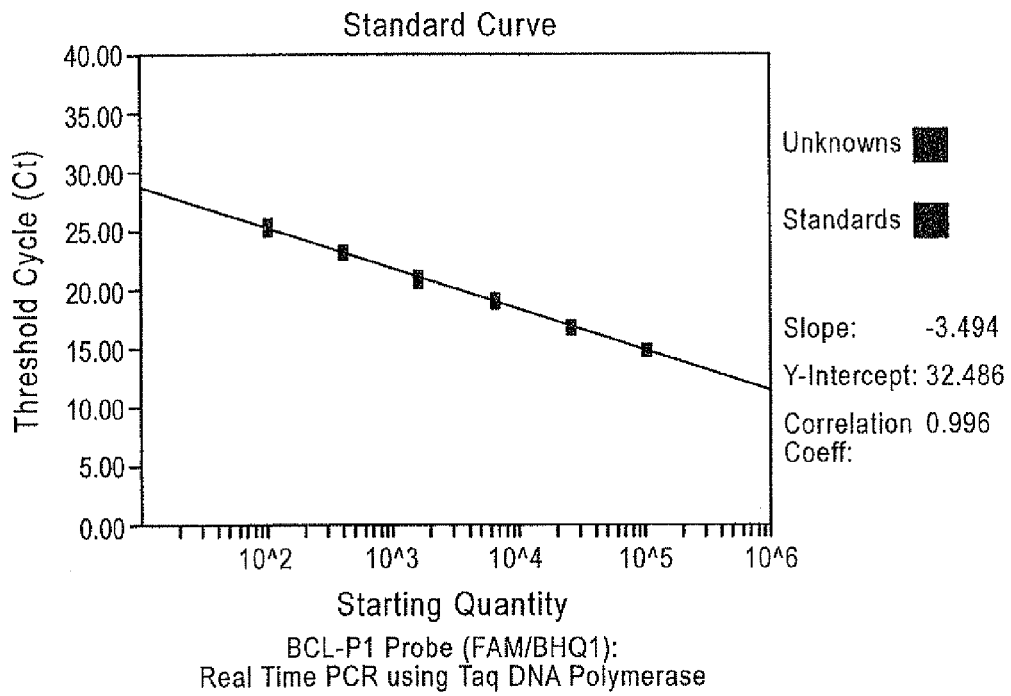
Figures 1, 2B:
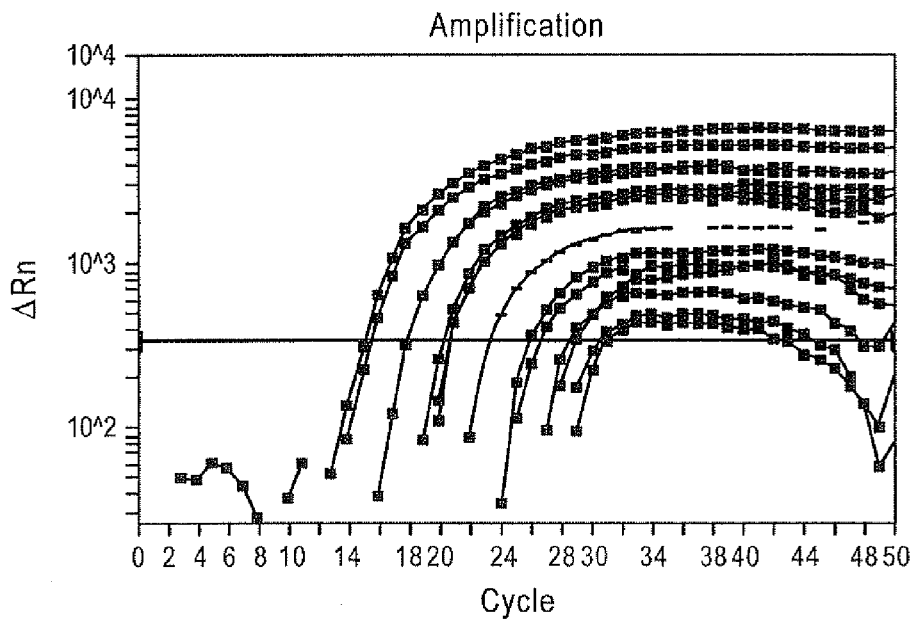
Figures 2, 2B:
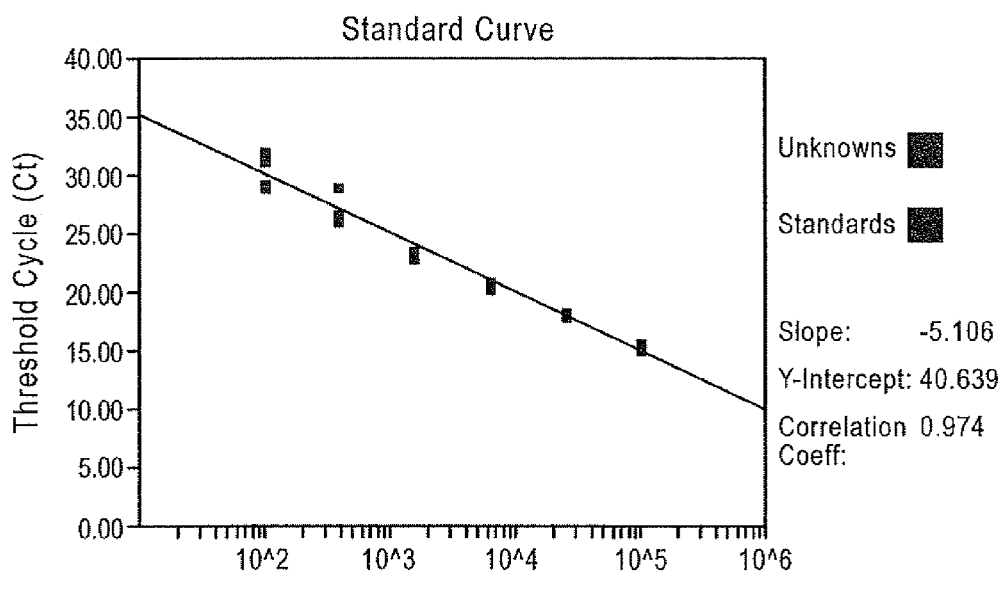
Figures 2, 2B, 3:
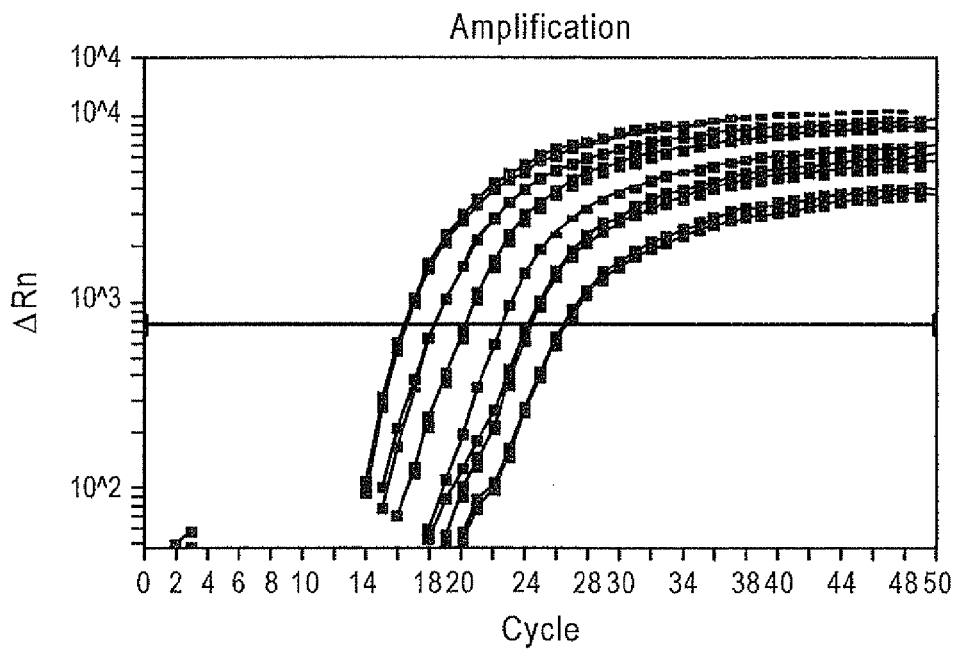
Figures 2, 2B, 3, 4:
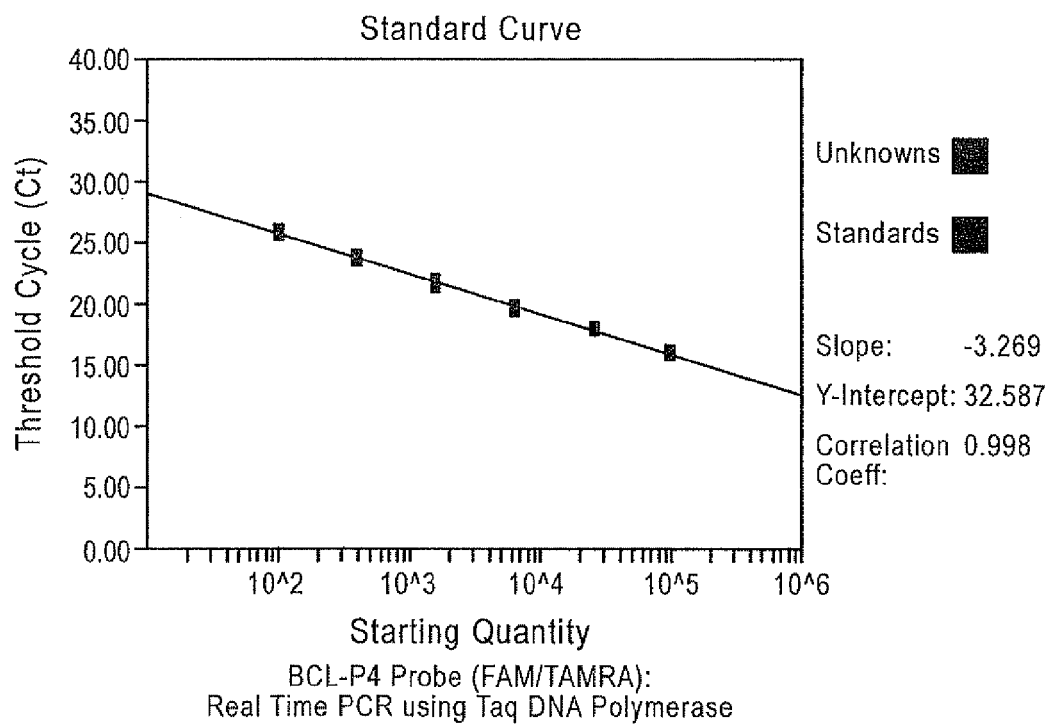
Figure 3A:
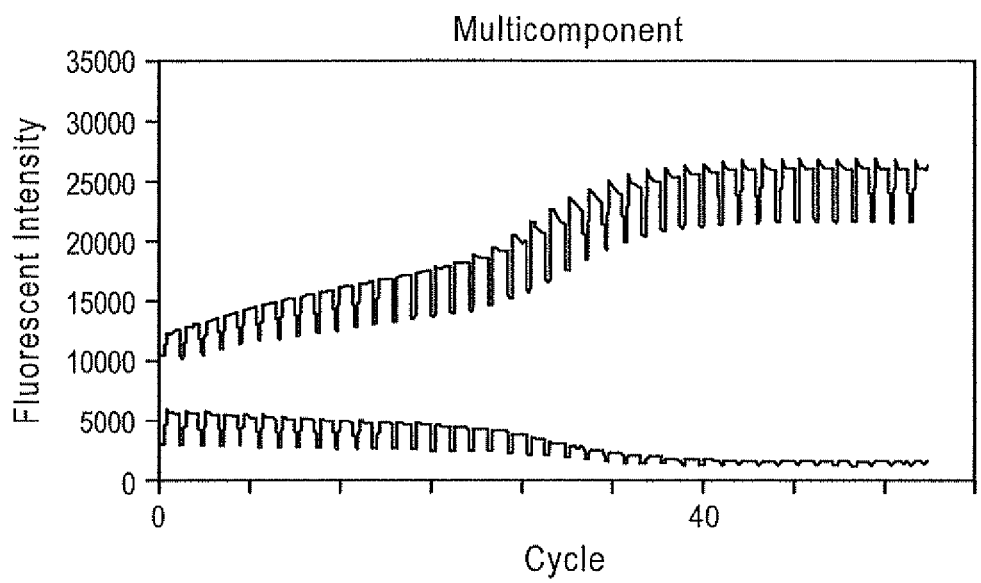
Figure 3B:
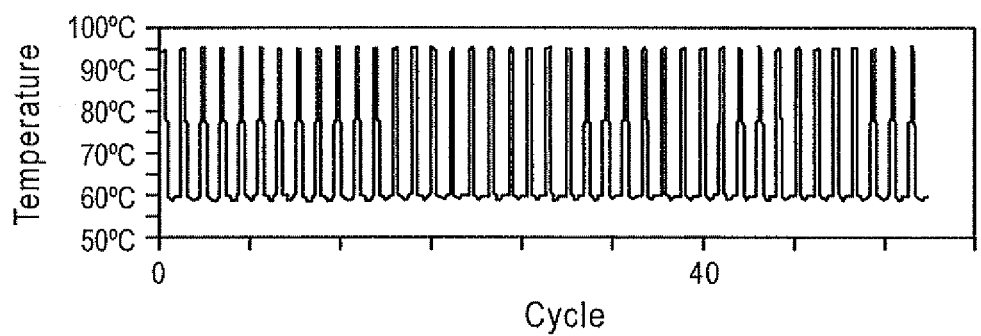
Figure 3C:
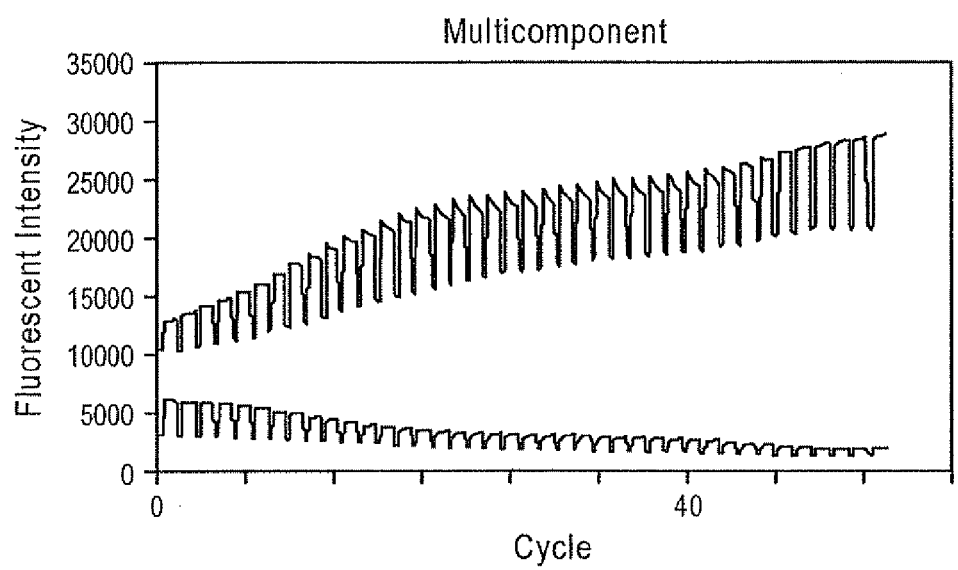
Figure 3D:
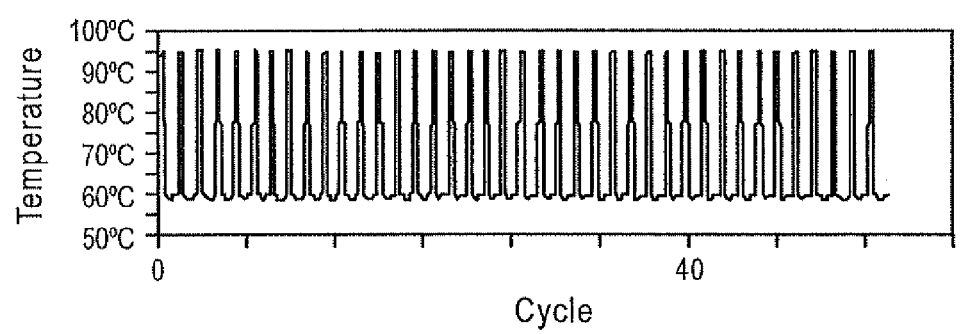
Figure 3E:
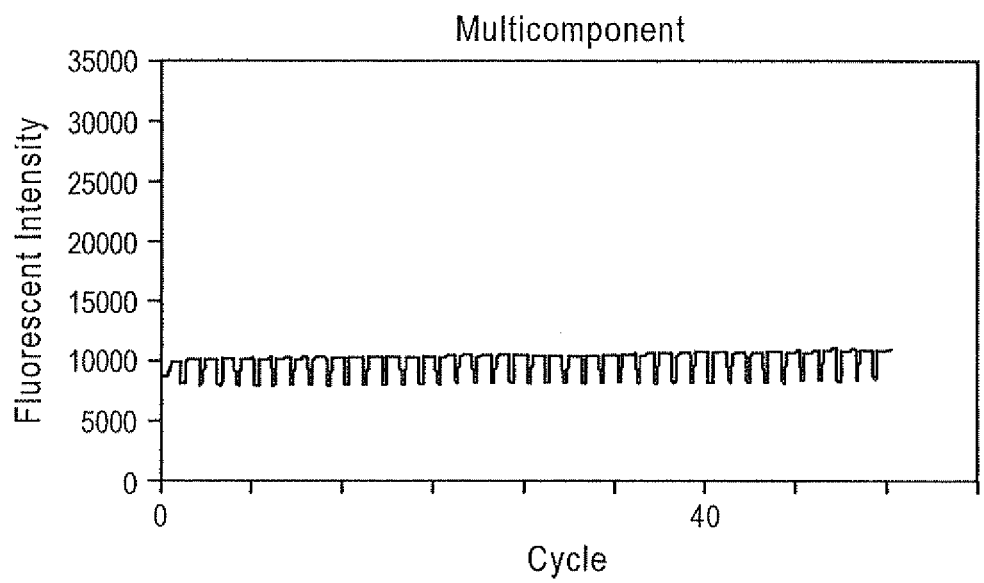
Figure 3F:
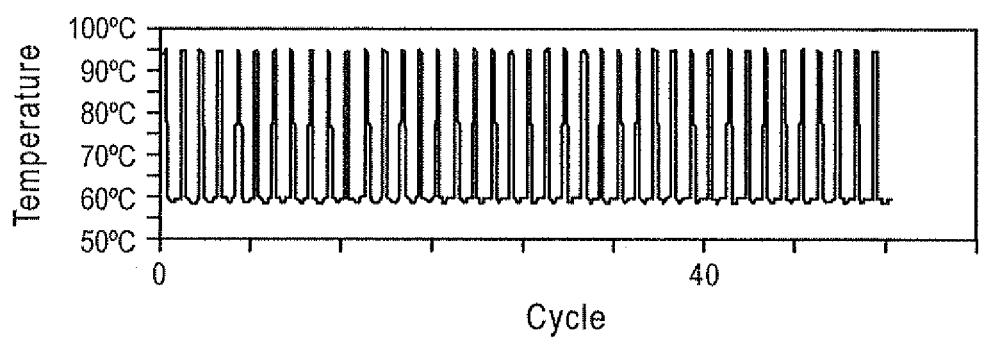
Figure 3G:
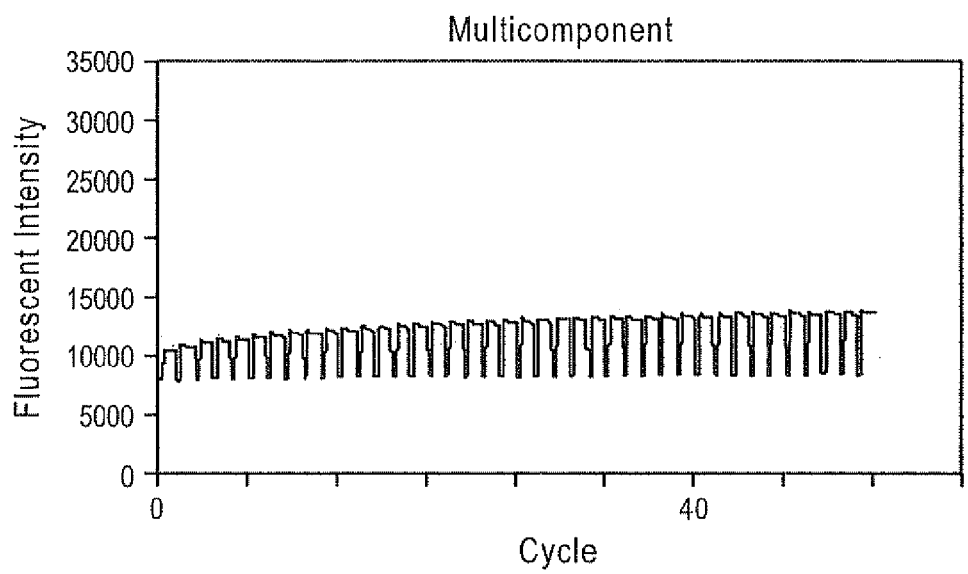
Figure 3H:
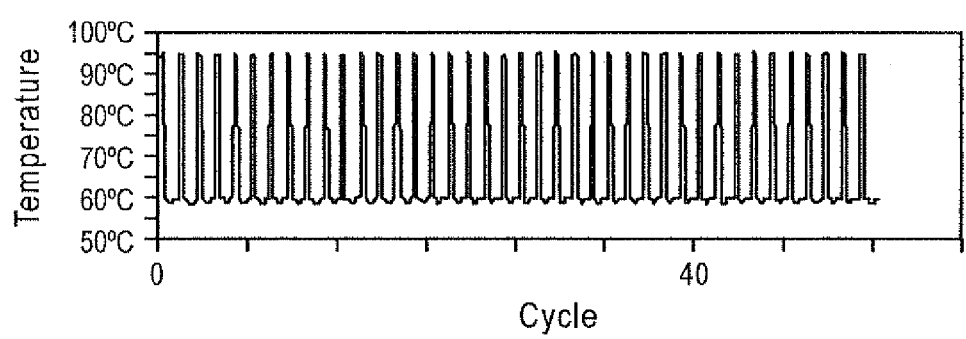
Figure 4:
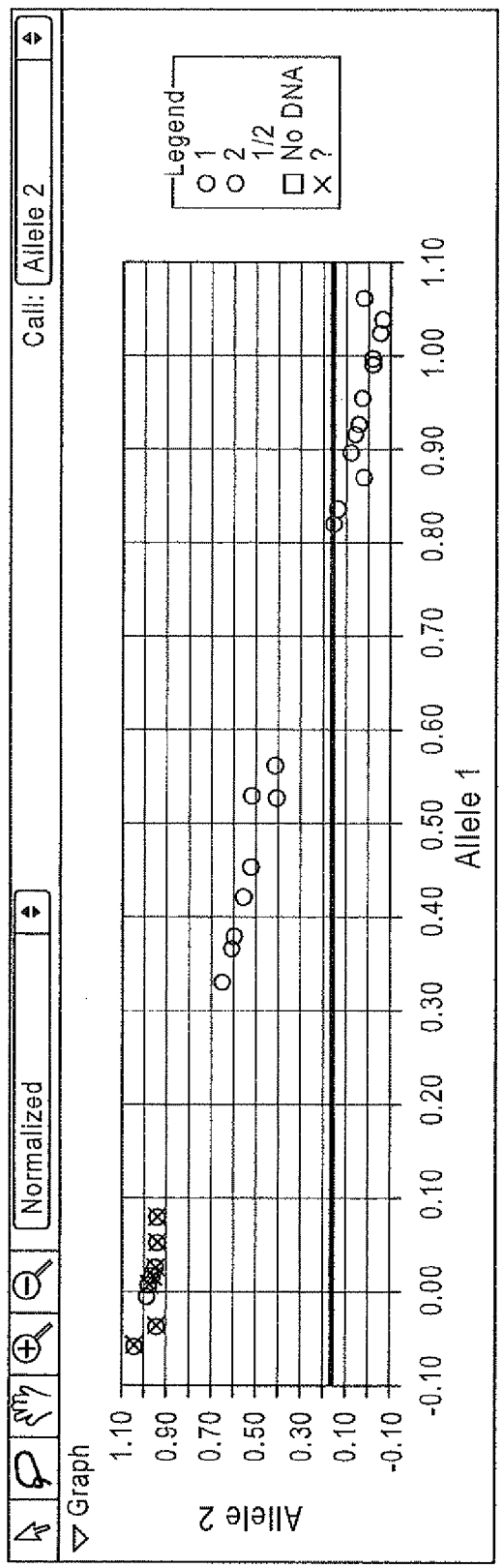

Representative Real Time amplification plot is shown in FIG. 2A-2B. FAM, labeled FET probes having either BHQ1 or Eclipse Dark Quencher at 3'-end are resistant to 3'→5' exonuclease, and are therefore suitable for use in high fidelity PCR (FIG. 2A). By contrast, FAM, labeled FET probes having either TAMRA or Dabcyl Quencher at 3'-end are degraded by 3'-5' exonuclease, and no proper real time PCR results can be obtained (FIG. 2B). Thus, similar results as Example 1 are repeated in a different system.

Example 3

Properties of FET Oligo as Primers

PCR amplifications were performed in ABI PRISM 7700 using 30 µl reactions that contained 10 mM Tris-HCl (pH8.85), 25 mM KCl, 5 mM $(NH_4)_2SO_4$, 5 mM $MgCl_2$, 0.2 mM dATP, 0.2 mM dTTP, 0.2 mM dGTP, 0.2 mM dCTP, 0.5 µM of each primer, 0.2 µM of each primer (ABCG-R1 and ABCG-P1 or ABCG-P2), 1 million copies of template (ABCG-T1) or just TE buffer in no template control (NTC), 0.6 units of Pwo DNA Polymerase (Roche Molecular Biochemicals). Thermal profile was 95° C. 10 sec; 40 cycles of 95° C. 15 sec, 60° C. 60 sec.

Example 4

Allele Discrimination Under High Fidelity PCR

An 89 basepair segment of the human methylenetetrahydrofolate reductase (MTHFR) gene was amplified using primers MTHFR-F1 and MTHFR-R1 listed in Table 1. Real Time amplifications and detection were performed in ABI PRISM 7700 using 30 µl reactions that contained 20 mM Tris-HCl (pH8.3), 60 mM KCl, 5.3 mM $MgCl_2$, 0.2 mM dATP, 0.2 mM dTTP, 0.2 mM dGTP, 0.2 mM dCTP, 0.1 uM of primer MTHFR-F1 and 1 µM of primer MTHFR-R1, 0.2 µM each of FET probes MTHFR-P1 and MTHFR-P2, templates containing varies number of MTHFR wild type or mutant or both as listed in table 4, a mix of Taq and Pwo DNA Polymerase (Roche Molecular Biochemicals) at unit ratio of 5 to 1. Thermal profile was 95° C. 15 sec; 50 cycles of 95° C. 15 sec, 55° C. 40 sec, 70° C. 40 sec. After amplification, fluorescent intensity at each well was measured by post PCR reading and analyzed by allele discrimination software in ABI PRISM 7700. Graphical result is shown in FIG. 4 and further summarized in Table 4.

TABLE 4

Summary of template types and allele call by PRISM 7700

| Template types (copy num) | Call by PRISM 7700 | Template types (copy num) | Call by PRISM 7700 | Template types (copy num) | Call by PRISM 7700 | Template types (copy num) | Call by PRISM 7700 |
|---|---|---|---|---|---|---|---|
| mut: $10^6$ | Allele 2 | mut: $2 \times 10^5$ wt: $10^5$ | Allele ½ | mut: $8 \times 10^3$ wt: $10^5$ | Allele 1 | Wt: $10^6$ | Allele 1 |
| mut: $10^6$ | Allele 2 | mut: $2 \times 10^5$ wt: $10^5$ | Allele ½ | mut: $8 \times 10^3$ wt: $10^5$ | Allele 1 | Wt: $10^6$ | Allele 1 |
| mut: $10^6$ | Allele 2 | mut: $2 \times 10^5$ wt: $10^5$ | Allele ½ | mut: $8 \times 10^3$ wt: $10^5$ | Allele 1 | Wt: $10^6$ | Allele 1 |
| mut: $10^6$ | Allele 2 | mut: $2 \times 10^5$ wt: $10^5$ | Allele ½ | mut: $8 \times 10^3$ wt: $10^5$ | Allele 1 | Wt: $10^6$ | Allele 1 |
| mut: $10^6$ wt: $10^5$ | Allele 2 | mut: $4 \times 10^4$ wt: $10^5$ | Allele ½ | mut: $1.6 \times 10^3$ wt: $10^5$ | Allele 1 | No template | No amp |
| Mut: $10^6$ wt: $10^5$ | Allele 2 | mut: $4 \times 10^4$ wt: $10^5$ | Allele ½ | mut: $1.6 \times 10^3$ wt: $10^5$ | Allele 1 | No template | No amp |

TABLE 4-continued

Summary of template types and allele call by PRISM 7700

| Template types (copy num) | Call by PRISM 7700 | Template types (copy num) | Call by PRISM 7700 | Template types (copy num) | Call by PRISM 7700 | Template types (copy num) | Call by PRISM 7700 |
|---|---|---|---|---|---|---|---|
| mut: $10^6$ wt: $10^5$ | Allele 2 | mut: $4 \times 10^4$ wt: $10^5$ | Allele ½ | mut: $1.6 \times 10^3$ wt: $10^5$ | Allele 1 | No template | No amp |
| mut: $10^6$ wt: $10^5$ | Allele 2 | mut: $4 \times 10^4$ wt: $10^5$ | Allele ½ | mut: $1.6 \times 10^3$ wt: $10^5$ | Allele 1 | No template | No amp |

Allele 1 = wild type (TET labeled probe)
Allele 2 = mutant type (FAM labeled probe)

The call by ABI PRISM 7700 matches well with types of template used (Table 4). No template controls give no amplification signal. Thus, two different allele sequences can be detected and distinguished using FAM and TET labeled FET probes under high fidelity PCR.

B. General

The oligonucleotides shown in Table 5 were used for the following example. Standard DNA phosphoramidites, including 6-carboxy-fluorescein (6-FAM) phosphoramidite, 5'-Tetrachloro-Fluorescein (TET) phosphoramidite, Acridine (ACR) phosphoramidite and 6-carboxytetramethyl-rhodamine (TAMRA) CPG, 3'-Dabcyl CPG, were obtained from Glen Research. Black Hole Quenchers (BHQ1) CPG were obtained from Biosearch Technology. Eclipse Dark Quencher (eDQ) CPG was obtained from Epoch Bioscience. All primers were purified using Oligo Purification Cartridges (Biosearch Technology). Doubly labeled FET probes were synthesized using CPGs with various quenchers as indicated in Table 5 and with either 6'FAM-labeled or TET-labeled phosphoramidites at the 5' end. The doubly labeled FET probes were purified by preparative HPLC and PAGE using standard protocols. Phosphorothioate modification was prepared by standard procedure. Minor groove binder netropsin and distamycin A were purchased from Sigma.

TABLE 5

| Name | | Type | Sequence |
|---|---|---|---|
| MTHFR-P1 | SEQ ID NO: 21 | Wt Probe | 5' TET- TGA AAT CGG CTC CCG CA -BHQ1-3' |
| MTHFR-P2 | SEQ ID NO: 22 | Mut Probe | 5' FAM- TGA AAT CGA CTC CCG CAG A -BHQ1-3' |
| MTHFR-P13 | SEQ ID NO: 23 | Wt Probe | 5' TET- TGA AAT CGG CTC CCG C -ACR-BHQ1-3' |
| MTHFR-P14 | SEQ ID NO: 24 | Wt Probe | 5' TET-ACR TGA AAT CGG CTC CCG C -BHQ1-3' |
| MTHFR-P3 | SEQ ID NO: 25 | Mut Probe | 5' FAM- TGA AAT CGA CTC CCG CAG -ACR-BHQ1-3' |

Example 6

Allele Discrimination Using Acridine-Labeled FET Probes Under High Fidelity PCR

An 89 basepair segment of the human methylenetetrahydrofolate reductase (MTHFR) gene was amplified using primers MTHFR-F1 and MTHFR-R1 listed in Table 1. Real Time amplifications and detection were performed in ABI PRISM 7700 using 30 µl reactions that contained 20 mM Tris-HCl (pH8.3), 60 mM KCl, 5.3 mM $MgCl_2$, 0.2 mM dATP, 0.2 mM dTTP, 0.2 mM dGTP, 0.2 mM dCTP, 0.15 uM of reference dye ROX, 0.5 uM each of primers MTHFR-F1 and MTHFR-R1, 0.2 µM each of FET probes, templates containing varies number of MTHFR wild type or mutant or both as listed in Table 6, a mix of Taq and Pwo DNA Polymerase (Roche Molecular Biochemicals) at unit ratio of 5 to 1. Five types of FET probes (MTHFR-P1, MTHFR-P2, MTHFR-P3, MTHFR-P13 and MTHFR-P14 as shown in Table 5) were tested in Real Time amplification. Thermal profile was 95° C. 15 sec; 50 cycles of 95° C. 15 sec, 57° C. 40 sec, 70° C. 40 sec.

Fluorescent intensity at each well was analyzed using real time data and software in ABI PRISM 7700 and summarized in Table 6. There was considerable cross-reactivity (or noise) between dyes FAM and TET (32% and 46% respectively) when normal FET probes were used. Such cross-reactivity was reduced to 2% and 4% when 3'-ACR labeled FET probes were used. However, 5'-ACR labeled FET probes did not show much difference to normal FET probes.

TABLE 6

Summary of probe and template types and ΔRn changes

| | Template types (copy num) | | |
| --- | --- | --- | --- |
| | wt: $10^6$  Mut: $10^6$ | | |
| | Fluorescent Intensity (ΔRn) | | |
| Probe Types | TET ΔRn | FAM ΔRn | % noise |
| 5' FAM- TGA AAT CGA CTC CCG CAG -ACR-BHQ1-3'<br>SEQ. ID No. 25 | 0.1 | 4.1 | 2% |
| 5' FAM- TGA AAT CGA CTC CCG CAG A -BHQ1-3'<br>SEQ. ID No. 22 | 1.4 | 4.4 | 32% |
| 5' TET- TGA AAT CGG CTC CCG C -ACR-BHQ1-3'<br>SEQ. ID No. 23 | 4.5 | 0.2 | 4% |
| 5' TET-ACR- TGA AAT CGG CTC CCG C -BHQ1-3'<br>SEQ. ID No. 24 | 2.7 | 0.8 | 30% |
| 5' TET- TGA AAT CGG CTC CCG CA -BHQ1-3'<br>SEQ. ID No. 21 | 5.4 | 2.5 | 46% |

Real Time amplifications and detection were further performed under the same conditions as above in ABI PRISM 7700 using 0.2 μM each of either normal or 3'-ACR-labeled FET probes as shown in Table 7 for allele discrimination. Real Time thermal profile was 95° C. 15 sec; 50 cycles of 95° C. 15 sec, 57° C. 40 sec, 70° C. 40 sec.

Fluorescent intensity of each dye at each well was analyzed using real time data and software in ABI PRISM 7700 and summarized in Table 6. There was considerable cross-reactivity (or noise) between dyes FAM and TET when normal FET probes were used. Such cross-reactivity was reduced to ~2% when 3'-ACR labeled FET probes were used. Because of much less cross-reactivity (or noise) between wt (TET) and mut (FAM) probes when using 3'-ACR-labeled FET probes, allelic analysis using 3'ACR-labeled probes was much closer to the theoretical prediction, therefore more accurate than using normal FET probe.

TABLE 7

Summary of probe and template types and allele discrimination results

| | | Template types (copy num) | | | | |
| --- | --- | --- | --- | --- | --- | --- |
| | | wt: $10^6$ | mut: $10^6$ | wt: $10^6$ +<br>mut: $10^6$ | wt: $10^6$ +<br>mut: $10^5$ | wt: $10^5$ +<br>mut: $10^6$ |
| Probe Types | | Fluorescent Intensity (ΔRn) | | | | |
| 5' FAM- TGA AAT CGA CTC CCG CAG A -BHQ1-3'<br>(SEQ ID NO: 22) + | FAM ΔRn | 0.7 | 5.4 | 3.8 | 1.4 | 5.3 |
| 5' TET- TGA AAT CGG CTC CCG CA -BHQ1-3'<br>(SEQ ID NO: 21) | TET ΔRn | 5.3 | 0.4 | 3.2 | 5.2 | 1.3 |
| % of dominant allele ΔRn to total ΔRn | | 88% | 93% | 54% | 79% | 80% |
| Theoretical % | | 100% | 100% | 50% | 91% | 91% |
| 5' FAM- TGA AAT CGA CTC CCG CAG -ACR-BHQ1-3'<br>(SEQ ID NO: 25) + | FAM ΔRn | 0.1 | 4.9 | 3.1 | 0.9 | 5.3 |
| 5' TET- TGA AAT CGG CTC CCG C -ACR-BHQ1-3'<br>(SEQ ID NO: 23) | TET ΔRn | 5.2 | 0.1 | 2.9 | 5.6 | 0.8 |
| % of dominant allele ΔRn to total ΔRn | | 98% | 98% | 52% | 86% | 87% |
| Theoretical % | | 100% | 100% | 50% | 91% | 91% |

The above results and discussion demonstrate that 3'-ACR labeled FET nucleic acid detectors suitable for use in high fidelity PCR for allele discrimination are provided by the subject invention. As such, the subject methods represent a significant contribution to the art.

Example 7

Allele Discrimination Using Free MGB Under High Fidelity Real Time PCR

An 89 basepair segment of the human methylenetetrahydrofolate reductase (MTHFR) gene was amplified using primers MTHFR-F1 and MTHFR-R1 listed in Table 1. Real Time amplifications and detection were performed in ABI PRISM 7700 using 30 µl reactions that contained 20 mM Tris-HCl (pH8.3), 60 mM KCl, 5.3 mM $MgCl_2$, 0.2 mM dATP, 0.2 mM dTTP, 0.2 mM dGTP, 0.2 mM dCTP, 0.15 uM of reference dye ROX, 0.5 uM each of primers MTHFR-F1 and MTHFR-R1, FET probes, plus or minus templates containing varies number of MTHFR wild type or mutant or both as listed in table 7, a mix of Taq and Pwo DNA Polymerase (Roche Molecular Biochemicals) at unit ratio of 5 to 1. In this test 0.2 µM each of either normal or 3'-ACR-labeled FET probes as shown in Table 7, plus or minus 0.4 µM free netropsin or distamycin A, were used for allele discrimination. Thermal profile was 95° C. 15 sec; 50 cycles of 95° C. 15 sec, 63° C. 40 sec, 70° C. 40 sec., or 95° C. 15 sec; 50 cycles of 95° C. 15 sec, 57° C. 40 sec, 70° C. 40 sec.

Similar results as Table 7 can be obtained at 63° C. anneal only when either free netropsin or distamycin A was included in PCR reaction mixture. There was no significant amplification when using normal PCR condition and 63° C. anneal.

Similar results as Table 7 were also obtained at 57° C. anneal with or without netropsin or distamycin A. The netropsin or distamycin A acted primarily to enhance oligo's Tm, especially of AT rich sequences, so that shorter oligos/probes can be used in real time PCR to enhance allele discrimination. Such features shall help primers/probes design for AT rich sequences.

The above results and discussion demonstrate that the inclusion of free netropsin or distamycin A in PCR mixture suitable for use in a variety of different high fidelity PCR applications are provided by the subject invention. As such, the subject methods represent a significant contribution to the art.

The above results and discussion demonstrate that FET labeled nucleic acid detectors suitable for use in a variety of different high fidelity PCR applications are provide by the subject invention. As such, the subject methods represent a significant contribution to the art.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

---

What is claimed is:

1. A FET labeled probe comprising a polycyclic nucleic acid intercalator bonded to a FET labeled oligonucleotide, wherein the oligonucleotide comprises a single-stranded target-binding sequence linked to a fluorophore and a dark quencher, and wherein the intercalator and the dark quencher are covalently bonded to the 3' terminus of the oligonucleotide.

2. The FET labeled probe according to claim 1, wherein the polycyclic nucleic acid intercalator comprises an aromatic ring.

3. The FET labeled probe according to claim 1, wherein the FET labeled oligonucleotide is selected from the group consisting of: a TAQMAN probe, a SCORPION probe, a SUNRISE probe, a molecular beacon, a conformationally assisted probe, and an in situ hybridization probe.

4. The FET labeled probe according to claim 1, wherein the dark quencher is a Black Hole Quencher.

5. The FET labeled probe according to claim 1, wherein the intercalator is covalently bonded to the oligonucleotide through at least one linker.

6. The FET labeled probe according to claim 1, wherein the intercalator is directly bonded to the 3' terminal nucleotide of the oligonucleotide.

7. The FET labeled probe according to claim 6, wherein the quencher is bonded to the intercalator.

8. The FET labeled probe according to claim 6, wherein the quencher is bonded to the 3' terminal nucleotide of the oligonucleotide.

9. A FET labeled probe comprising a polycyclic nucleic acid intercalator bonded to a FET labeled oligonucleotide, wherein the oligonucleotide comprises a single-stranded target-binding sequence linked to a fluorophore and a quencher, wherein the intercalator and the quencher are covalently bonded to the 3' terminus of the oligonucleotide, and wherein the oligonucleotide is selected from the group consisting of: a TAQMAN probe, a SCORPION probe, a SUNRISE probe, a molecular beacon, a conformationally assisted probe, and an in situ hybridization probe.

10. The FET labeled probe according to claim 9, wherein the intercalator is covalently bonded to the oligonucleotide through at least one linker.

11. The FET labeled probe according to claim 9, wherein the intercalator is directly bonded to the 3' terminal nucleotide of the oligonucleotide.

12. The FET labeled probe according to claim 11, wherein the quencher is bonded to the intercalator.

13. The FET labeled probe according to claim 11, wherein the quencher is bonded to the 3' terminal nucleotide of the oligonucleotide.

14. A probe comprising a polycyclic nucleic acid intercalator bonded to a FET labeled oligonucleotide, wherein the oligonucleotide comprises a single-stranded target-binding sequence linked to a fluorophore and a dark quencher, and wherein the intercalator and the quencher extend from the 3' terminal nucleotide of the oligonucleotide.

15. The probe according to claim 14, wherein the intercalator extends from the oligonucleotide through at least one linker.

16. The probe according to claim 14, wherein the intercalator extends directly from the 3' terminal nucleotide.

17. The probe according to claim 16, wherein the quencher extends from the intercalator.

18. The probe according to claim 14, wherein the quencher extends from the oligonucleotide through at least one linker.

19. The probe according to claim 14, wherein the quencher extends directly from the 3' terminal nucleotide.

20. The probe according to claim 19, wherein the intercalator extends from the quencher.

\* \* \* \* \*